(12) United States Patent
Cork et al.

(10) Patent No.: US 10,431,335 B2
(45) Date of Patent: Oct. 1, 2019

(54) MOBILE APPLICATIONS FOR MEDICAL DEVICES

(71) Applicant: Fenwal, Inc., Lake Zurich, IL (US)

(72) Inventors: William H. Cork, Lake Bluff, IL (US); Brian C. Case, Lake Villa, IL (US); Jonathan Prendergast, Palatine, IL (US); John W. Barry, Mount Prospect, IL (US)

(73) Assignee: Fenwal, Inc., Lake Zurich, IL (US)

( * ) Notice: Subject to any disclaimer, the term of this patent is extended or adjusted under 35 U.S.C. 154(b) by 764 days.

(21) Appl. No.: 13/748,580

(22) Filed: Jan. 23, 2013

(65) Prior Publication Data

US 2013/0138452 A1 May 30, 2013

Related U.S. Application Data

(63) Continuation-in-part of application No. 13/209,161, filed on Aug. 12, 2011.
(Continued)

(51) Int. Cl.
*G16H 40/63* (2018.01)
*G06Q 10/08* (2012.01)
(Continued)

(52) U.S. Cl.
CPC ......... *G16H 40/63* (2018.01); *G06F 19/3418* (2013.01); *G06Q 10/087* (2013.01);
(Continued)

(58) Field of Classification Search
CPC ............... G06F 19/3468; G06F 19/322; G06F 19/3406; G06F 19/327; G06F 19/00; A61M 2205/18; A61B 5/14532; A61B 5/14546
(Continued)

(56) References Cited

U.S. PATENT DOCUMENTS 4,605,503 A 8/1986 Bilstad et al.
5,153,827 A 10/1992 Coutre
(Continued)

FOREIGN PATENT DOCUMENTS

EP 1924307 B1 4/2012
EP 2624157 8/2013
(Continued)

OTHER PUBLICATIONS

Final Rejection dated Sep. 25, 2013 in U.S. Appl. No. 13/209,161.
(Continued)

*Primary Examiner* — Victoria P Augustine
*Assistant Examiner* — Teresa S Williams
(74) *Attorney, Agent, or Firm* — Becker Patent Law, LLC

(57) ABSTRACT

Certain examples provide systems, methods, and apparatus to provide information regarding medical devices via a mobile device. An example method for mobile medical device management includes providing a representation of one or more medical devices with a visual indication of a status for each device. The representation is to visually convey information regarding each of the one or more medical devices and is selectable by a user to provide additional information regarding each of the one or more medical devices. The method includes facilitating interaction with the one or more medical devices via the mobile device. The method includes dynamically updating the status for each medical device via communication between the mobile device and one or more facilities at which the one or more medical devices are located.

16 Claims, 14 Drawing Sheets

Related U.S. Application Data

(60) Provisional application No. 61/637,694, filed on Apr. 24, 2012, provisional application No. 61/589,755, filed on Jan. 23, 2012, provisional application No. 61/383,174, filed on Sep. 15, 2010, provisional application No. 61/373,197, filed on Aug. 12, 2010.

(51) Int. Cl.
  *G06Q 50/22* (2018.01)
  *G06T 11/20* (2006.01)
  *G06F 19/00* (2018.01)
  *G06Q 10/10* (2012.01)
  *G16H 10/60* (2018.01)

(52) U.S. Cl.
  CPC ......... *G06Q 10/1093* (2013.01); *G06Q 50/22* (2013.01); *G06T 11/206* (2013.01); *G16H 10/60* (2018.01)

(58) Field of Classification Search
  USPC .......... 128/845; 600/300; 705/2, 3; 709/217; 715/771
  See application file for complete search history.

(56) References Cited

U.S. PATENT DOCUMENTS

| | | | |
|---|---|---|---|
| 6,256,643 | B1 | 7/2001 | Cork et al. |
| 6,488,029 | B1* | 12/2002 | Hood ................ A61G 1/00 128/845 |
| 6,540,672 | B1 | 4/2003 | Simonsen |
| 6,542,910 | B2 | 4/2003 | Cork et al. |
| 6,571,128 | B2 | 5/2003 | Lebel et al. |
| 6,602,469 | B1 | 8/2003 | Maus et al. |
| 6,613,566 | B2 | 9/2003 | Kandler et al. |
| 6,635,014 | B2 | 10/2003 | Starkweather et al. |
| 6,671,563 | B1 | 12/2003 | Engelson et al. |
| 7,225,406 | B2* | 5/2007 | Babula et al. ............... 715/736 |
| 7,300,418 | B2 | 11/2007 | Zaleski |
| 7,384,410 | B2 | 6/2008 | Eggers et al. |
| 7,815,602 | B2 | 10/2010 | Mann et al. |
| 7,861,122 | B2 | 12/2010 | Cornwell et al. |
| 7,942,844 | B2 | 5/2011 | Moberg et al. |
| 8,038,593 | B2 | 10/2011 | Friedman et al. |
| 8,229,535 | B2 | 7/2012 | Mensinger et al. |
| 8,234,128 | B2 | 7/2012 | Martucci et al. |
| 8,255,238 | B2 | 8/2012 | Powell et al. |
| 8,285,328 | B2 | 10/2012 | Caffey et al. |
| 8,291,337 | B2* | 10/2012 | Gannin ................. A61M 5/172 715/771 |
| 8,485,828 | B2 | 7/2013 | Cork et al. |
| 8,552,880 | B2 | 10/2013 | Kopp |
| 8,645,154 | B2 | 2/2014 | Eggers et al. |
| 8,676,600 | B2 | 3/2014 | Case et al. |
| 9,727,696 | B2 | 8/2017 | Case et al. |
| 2001/0044731 | A1 | 11/2001 | Coffman et al. |
| 2003/0004758 | A1* | 1/2003 | Luttrell ............................. 705/3 |
| 2003/0040835 | A1 | 2/2003 | Ng |
| 2003/0040938 | A1 | 2/2003 | Ng et al. |
| 2003/0093503 | A1 | 5/2003 | Yamaki et al. |
| 2006/0031098 | A1 | 2/2006 | Kalthoff et al. |
| 2006/0100746 | A1* | 5/2006 | Leibner-Druska ............ 700/282 |
| 2006/0116639 | A1* | 6/2006 | Russell ......................... 604/131 |
| 2006/0229557 | A1* | 10/2006 | Fathallah et al. ............. 604/131 |
| 2007/0165827 | A1 | 8/2007 | Wariar |
| 2007/0219826 | A1 | 9/2007 | Brodsky et al. |
| 2008/0033744 | A1 | 2/2008 | Jones |
| 2008/0126969 | A1* | 5/2008 | Blomquist ..................... 715/771 |
| 2008/0172026 | A1 | 7/2008 | Blomquist |
| 2009/0076856 | A1 | 3/2009 | Darby et al. |
| 2009/0153058 | A1* | 6/2009 | Feng et al. ..................... 315/76 |
| 2009/0156991 | A1 | 6/2009 | Roberts |
| 2009/0163855 | A1 | 6/2009 | Shin |
| 2009/0177992 | A1* | 7/2009 | Rubalcaba et al. ........... 715/771 |
| 2009/0217202 | A1 | 8/2009 | Foley et al. |
| 2009/0259408 | A1 | 10/2009 | Mishima et al. |
| 2009/0259493 | A1 | 10/2009 | Venon et al. |
| 2009/0276345 | A1 | 11/2009 | Hughes |
| 2010/0049542 | A1 | 2/2010 | Benjamin et al. |
| 2010/0131883 | A1* | 5/2010 | Linthicum et al. ........... 715/771 |
| 2011/0137134 | A1* | 6/2011 | Hemmerling et al. ....... 600/301 |
| 2011/0185035 | A1* | 7/2011 | Van ............................... 709/217 |
| 2011/0295749 | A1 | 12/2011 | Scalisi |
| 2012/0038651 | A1 | 2/2012 | Case et al. |
| 2012/0041777 | A1 | 2/2012 | Case et al. |
| 2012/0271655 | A1 | 10/2012 | Knobel et al. |
| 2014/0276571 | A1 | 9/2014 | Ludolph et al. |
| 2014/0298022 | A1 | 10/2014 | Proennecke et al. |

FOREIGN PATENT DOCUMENTS

| | | |
|---|---|---|
| WO | WO2002080993 | 10/2002 |
| WO | 2012075322 | 6/2012 |

OTHER PUBLICATIONS

Response to Office Action, dated Jul. 24, 2013, in U.S. Appl. No. 13/209,161.
Non-final Office Action dated Apr. 24, 2013 in U.S. Appl. No. 13/209,161.
Velasco, Anna "Birmingham Firm's Software Aid Doctors Keep Track of Patients' Vital Signs," Everything Alabama, http://blog.al.com/living-news//print.html, Dec. 24, 2009.
Looking Glass, "iGive Blood," iTunes App Store, http://itunes.apple.com/us/app/igive-blood/id330741267?mt=8, (Last Accessed Aug. 28, 2012).
Notification Concerning Transmittal of International Preliminary Report on Patentability (IPRP), IPRP and Written Opinion of the International Searching Authority, International application No. PCT/US2013/022736, seven pages.
Non-Final Office Action in U.S. Appl. No. 13/209,161 dated Mar. 3, 2015.
Reply to Non-Final Office Action in U.S. Appl. No. 13/209,161 dated Jun. 3, 2015.
"Go for the Gold" website: (www.goforthegold.org) May 30, 2009.
"The Blood Alliance" website (www.igiveblood.com) May 28, 2010.
"The Blood Center" website; (www.thebloodcenter.org) May 14, 2010.
"Blood Battle" website: (www.umich.edu/bloodbat/history.html).
"iGive Blood on the App Store on iTunes," printed from https://itunes.apple.com/us/app/igive-blood/id330741267?mt=8, Jun. 3, 2015.
Argument from Pre-Appeal Brief Conference Request, U.S. Appl. No. 13/209,161, dated Dec. 21, 2016, 5 pages.
Final Office Action, U.S. Appl. No. 13/209,161 dated Sep. 21, 2016, 37 pages.
Notice of Allowance in U.S. Appl. No. 13/209,161 dated Nov. 6, 2013, 10 pages.
European Search Report and Opinion from EP App. No. 13152417.5, dated Apr. 20, 2016, 9 pages.
Non-Final Office Action in U.S. Appl. No. 13/209,161 dated Aug. 24, 2018, 29 pages.
Appeal Brief Filed in U.S. Appl. No. 13/209,161 dated Jan. 29, 2019, 37 pages.
Appeal Brief Filed in U.S. Appl. No. 13/209,161 dated Jan. 22, 2018, 30 pages.
Advisory Action in U.S. Appl. No. 13/209,161 dated Oct. 17, 2017, 3 pages.
Non-Final Office Action in U.S. Appl. No. 13/209,161 dated Jan. 15, 2016, 29 pages.
Non-Final Office Action in U.S. Appl. No. 14/971,707 dated Oct. 11, 2016, 28 pages.

\* cited by examiner

Op C

MOBILE APPLICATIONS FOR MEDICAL DEVICES

CROSS-REFERENCE TO RELATED APPLICATIONS

The present application relates and claims priority to U.S. Provisional Patent Application Ser. No. 61/589,755, filed on Jan. 23, 2012, U.S. Provisional Patent Application Ser. No. 61/637,694, filed on Apr. 24, 2012, and as a continuation-in-part of U.S. patent application Ser. No. 13/209,161, filed on Aug. 12, 2011, which claims priority to U.S. provisional patent application Ser. No. 61/373,197, filed on Aug. 12, 2010, and U.S. provisional patent application, Ser. No. 61/383,174, filed on Sep. 15, 2010, each of which is herein incorporated by reference in its entirety.

FIELD

The present disclosure relates generally to medical devices. More specifically, the present disclosure relates to methods, systems, and apparatus to provide mobile applications for medical devices.

BACKGROUND

Increasingly, medical devices are becoming electronic or involve an electronic or software component. Electronic devices, distributed facilities, and scattered patients make training, treatment, and troubleshooting difficult. Further, it is often difficult to educate the public, and patients may not seek the treatment they should due to a lack of information and access. Operators and administrators may also introduce inefficiencies in their operation and management of medical devices due to a lack of information and access.

BRIEF SUMMARY

Certain examples provide systems, methods, and apparatus to provide information and control for one or more medical devices via a mobile device.

Certain examples provide a computer-implemented method for medical device management using a mobile device. The example method includes providing, via a mobile device interface, a representation of one or more medical devices with a visual indication of a status for each medical device, the representation visually conveying information regarding each of the one or more medical devices and selectable by a user to provide additional information regarding each of the one or more medical devices. The example method includes facilitating interaction with the one or more medical devices via the mobile device. The example method includes dynamically updating the status for each medical device via communication between the mobile device and one or more facilities at which the one or more medical devices are located.

Certain examples provide a tangible computer readable storage medium including program code for execution by a processor, the program code, when executed, to implement a method for medical device management using a mobile device. The example method includes providing, via a mobile device interface, a representation of one or more medical devices with a visual indication of a status for each medical device, the representation visually conveying information regarding each of the one or more medical devices and selectable by a user to provide additional information regarding each of the one or more medical devices. The example method includes facilitating interaction with the one or more medical devices via the mobile device. The example method includes dynamically updating the status for each medical device via communication between the mobile device and one or more facilities at which the one or more medical devices are located.

Certain examples provide a system to control a drug delivery device via a mobile device. The example system includes a processing circuit operable to provide, via a mobile device interface, a visual indication of a status for a drug delivery device, the visual indication conveying information regarding the drug delivery device and selectable by a user to provide additional information regarding the drug delivery device. The example processing circuit is operable to facilitate interaction with the drug delivery device via the mobile device. The example processing circuit is operable to dynamically update the status for the drug delivery device via communication between the drug delivery device and the mobile device.

Figure 1:
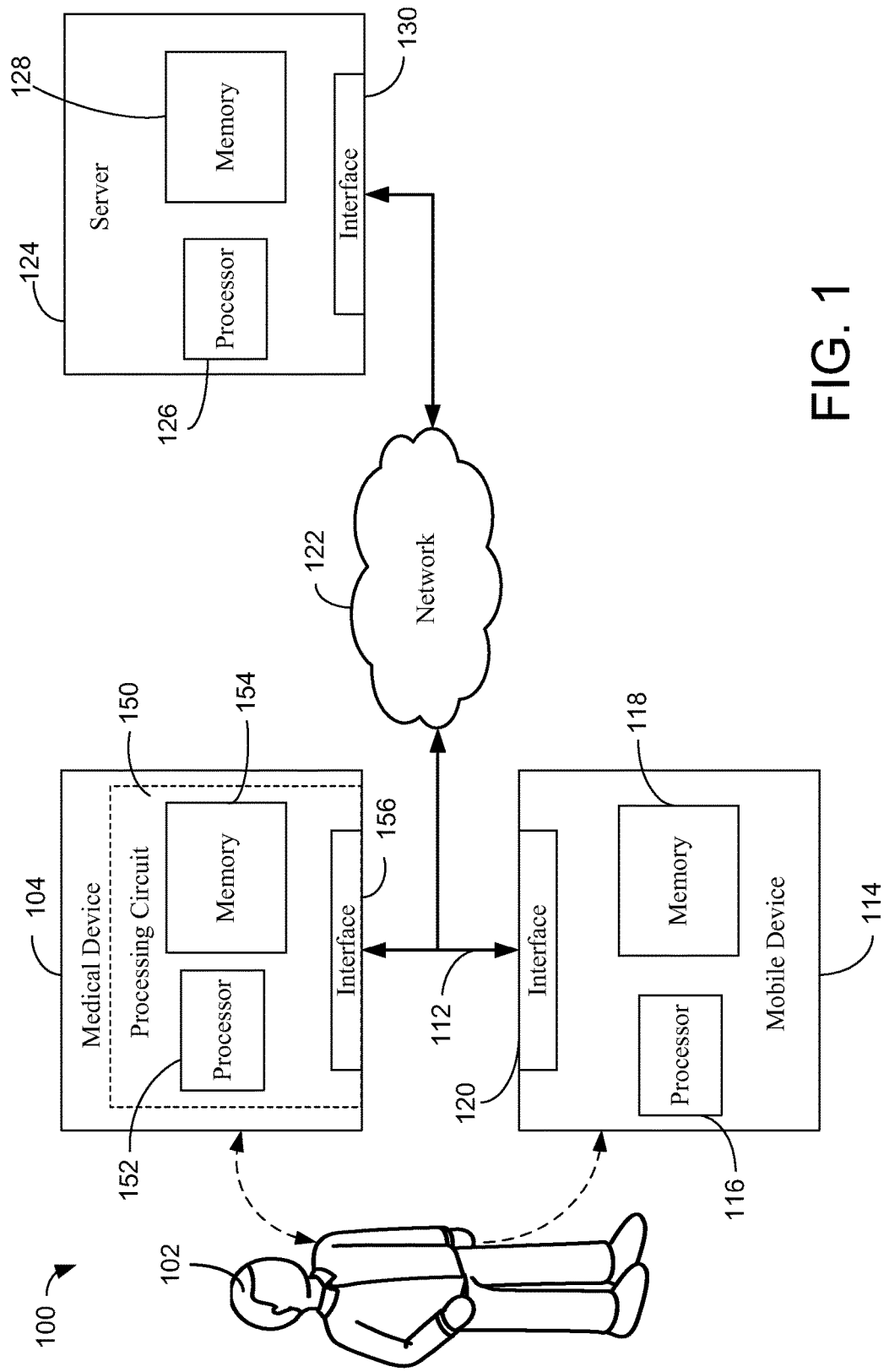
FIG. 1 is a block diagram of an example computing system.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DESCRIPTION OF CERTAIN EXAMPLES

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

It will be understood that the present invention may be embodied in other specific forms without departing from the spirit thereof. The present examples and embodiments, therefore, are to be considered in all respects as illustrative and not restrictive, and the invention is not to be limited to the details presented herein.

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Certain examples provide mobile applications for medical devices including blood collection or apheresis devices, infusion pumps, drug delivery pumps, and/or other medical devices. For example, an infusion pump infuses fluids, medication, or nutrients into a patient. An infusion pump can be used intravenously, subcutaneously, arterially, and/or epidurally, for example. For example, an infusion pump can administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In certain examples, an operator (e.g., a technician, nurse, etc.) provides input regarding type of infusion, mode, and/or other device parameter. For example, continuous infusion provides small pulses of infusion (e.g., between 500 nanoliters and 10 milliliters), with a pulse rate based on a programmed infusion speed. Intermittent infusion alternates between a high infusion rate and a low infusion rate with timing programmable to keep a cannula open, for example. Patient-controlled infusion provides on-demand infusion with a preprogrammed ceiling to avoid patient intoxication. The infusion rate is controlled by a pressure pad or button that can be activated by the patient, for example. Infusion pumps can include large volume pumps (e.g., for nutrient solution delivery to feed a patient), small-volume pumps (e.g., for medicine delivery), etc.

Certain examples provide patient, administration, operations, and/or service applications. Certain examples converge information into one application that helps provide improved record keeping, better user experience, reduction of waste, and/or enhanced ease of use for the user, for example. In addition, flow of communication can be improved throughout the supply chain. Furthermore, certain examples help provide for automation of manual tasks which would eliminate or reduce potential user errors.

In certain examples, an application can provide training, feedback, monitor, and status information on a medical device operation, such as a collection (e.g., apheresis) or delivery (e.g., infusion) process. For example, an application on a mobile or handheld computing device (e.g., an Apple IPAD™, IPHONE™, and/or other tablet computer or smartphone) can help facilitate user training with respect to one or more medical devices and/or associated procedures. For example, use of equipment and supplies may be facilitated.

In certain examples, a customer may purchase an application and/or download the application to a device. Materials may be provided to explain the application, provide directions for downloading/installing the application onto a phone or other mobile device (e.g., other mobile computer), and/or explain how to use the application. In some examples, an application can give visual assistance in operating a medical device such as a blood collection instrument or drug delivery system. In some examples, the application may provide a mobile version of the operator's manual for the medical device.

In some examples, an application may make provider websites mobile-friendly. For example, Microsoft SHAREPOINT™ supports mobile views and can be leveraged to provide a mobile-friendly provider (e.g., Fenwal) website.

In some examples, an application for use with a mobile device is integrated with a provider (e.g., Fenwal) data management system. In some examples, the application enables the device to be made 21 CFR part 11 compliant. In some examples, the application can be used across a variety of blood products and/or drugs for delivery.

In certain examples, an application can provide feedback on a component collection or drug delivery process. The application can diagram the procedure, for example. In certain examples, another part of the application can monitor flow rates (e.g., range, accuracy, etc.), physiological data, volume limits, pressure, power (e.g., battery), pressure variation and/or limit, occlusion checking, bolus (and/or bolus reduction), starting, stopping, ramp up, ramp down, induction/loading dose, infusion time, infusion mode (micro-infusion or macro-infusion), line check, device check, drug name, etc., and provide feedback to a user via a mobile device. The application can facilitate diagnostics, reporting, and/or control remotely (e.g., throughout a hospital or other site via mobile device). The application can provide a customized drug library, infusion history management, hypnotic and analgesic effects management, disposables tracking, etc., across a variety of infusion and/or other drug delivery or blood collection/transfusion protocols.

In certain examples, a medical device (e.g., blood collection/processing machine, infusion pump or other drug delivery system, etc.) communicates with a user's mobile device (e.g., a phone) based on one or more criterion such as user characteristic(s) and/or user location. Compliance with rules, guidelines, best practices, etc., can be facilitated via a mobile application.

According to various aspects of the present disclosure, physiological data may be integrated into a medical device used to perform a medical procedure on a patient. In some implementations, the integrated physiological data may be used by the medical device to create an electronic record of the medical procedure. For example, the physiological data and performance characteristics of the medical device may be time stamped during the procedure to record how the patient reacted to different operational states of the medical device. In some cases, the electronic records may be sent to a central server for further data storage and processing. In further implementations, the integrated physiological data may be used by the medical device to generate alerts. For example, an alert may be generated if the patient's blood pressure drops below an acceptable threshold during the medical procedure. In further implementations, the medical device may be configured to automatically adjust one or more of its operating parameters based in part on the physiological data.

According to various implementations, data used in a medical device, such as an apheresis machine or infusion pump, may also be stored in segregated memory locations. In some implementations, different read/write permissions may be applied to the memory locations based on the operational state of the medical device. For example, a first memory location may store a routine that causes the device to perform a medical procedure and a second memory location may store operational data regarding the operation of the medical device. During execution of the routine, the first memory location may be allowed to write data to the second memory location. For example, the routine may be able to transfer data regarding the medical procedure to the second memory location. However, the second memory location may be prevented from writing data to the first memory location during performance of the medical procedure. Thus, the first memory location may be protected from potential sources of failure during the medical procedure. Once the routine stops executing and the medical procedure concludes, the second memory location may be able to write data to the first memory location. For example, an update for the routine stored at the second memory location may be installed to the first memory location, if the device is not being used to perform a medical procedure.

Any data that is not critical to the execution of a routine that performs a medical procedure may be stored in a separate memory location from the routine. In some implementations, the non-critical data may include operational data for the medical device. Operational data may include, but is not limited to, diagnostic data, debugging data, log data indicative of activities conducted during the apheresis procedure, and other such data. Other example forms of data that may not be critical to the performance of a medical procedure include communication routines (e.g., to receive and/or transfer data from the medical device to another electronic device), update routines (e.g., to update a routine that performs a medical procedure, to update a communication routine, etc.), and physiological measurements taken from a living subject.

Memory locations in a medical device may also be mirrored or synchronized, to provide redundant data storage. For example, a routine that causes the device to perform a medical procedure may be stored in redundant memory locations (e.g., the contents of a first memory location may be mirrored to one or more other memory locations). In some cases, the redundant memory locations may be stored on separate memory devices (e.g., data storage devices that are physically separated). For example, copies of a routine may be mirrored across two or more different hard disks. If a disk failure occurs, the routine may continue to execute by running from the mirrored hard disk.

Referring now to FIG. 1, an exemplary computer system 100 is shown. Computer system 100 may be used in a medical setting to perform a medical procedure involving subject 102. System 100 includes a medical device 104 configured to perform the medical procedure and a mobile device 114, configured to communicate with the medical device 104 to monitor operation of the medical device 104, control the medical device 104, etc. In some implementations, mobile device 114 and/or medical device 104 may communicate via network 122 with a server 124 before, during, and/or after the medical procedure is performed. For example, medical device 104 may transmit data via network 122 regarding the performance of the procedure to server 124 (e.g., the subject's physical state, the operational states of medical device 104, etc.). Similarly, server 124 may transmit data via network 122 to medical device 104, such as a routine to load or update existing software on medical device 104, subject data regarding subject 102 (e.g., the patient's medical history, chart information, etc.), and other operational data.

Medical device 104 may be any form of electronic device configured to perform a medical procedure on subject 102. In non-limiting examples, medical device 104 may be a device that administers a medicament to subject 102, extracts fluid or tissue from subject 102, implants an object into subject 102, or captures a medical image of subject 102. For example, medical device 104 may be a dialysis machine (e.g., a hemodialysis machine, a hemofiltration machine, etc,), an infusion pump, or a drug delivery system, in some implementations. In various implementations, medical device 104 may be an apheresis machine configured to draw blood from subject 102 (i.e., subject 102 is a donor or receiver of blood components). In some implementations, medical device 104 may use measurements taken from subject 102 to control the medical procedure. The measurements may be taken directly by medical device 104 or may be received by medical device 104 via data link 112 from a measurement device. For example, medical device 104 may use the body temperature, pulse rate, blood pressure, respiratory rate, blood glucose level, pupil dilation, pulse oximetry information, ECG information, or other physical characteristic of subject 102 during the medical procedure.

Mobile device 114 may be any form of handheld or portable electronic device configured to communicate with the medical device 104 (e.g., to receive information from and/or provide information to the medical device 104 for control, reporting, etc.).

Medical device 104 may include a processor 152, a memory 154, and an interface 156 (e.g., a processing circuit 150). Processor 152 may include one or more microprocessors, application-specific integrated circuits (ASICs), field programmable gate arrays (FPGAs), other forms of processing components, or a combination thereof. Memory 154 may include any form of electronic, optical, magnetic, or other form of data storage configured to provide processor 152 with program instructions. Memory 154 may further include a floppy disk, CD-ROM, DVD, magnetic disk, memory chip, ROM, RAM, EEPROM, EPROM, flash memory, optical media, other forms of non-transitory media, or any other suitable memory from which processor 152 can read instructions. When executed by processor 152, the instructions cause medical device 104 to perform some or all of the functions described herein. In various implementations, data stored in memory 154 may be segregated across different memory locations (e.g., in different memory storage devices, in different partitions of the same storage device, etc.). Data in memory 154 may also be stored redundantly, in some implementations. For example, data may be mirrored in memory 154 to a plurality of memory storage devices, allowing for continuous operation of medical device 104, if one of the storage devices experiences a failure.

Medical device 104 may include interface 156 configured to receive and/or transmit data to other electronic devices. For example, medical device 104 may utilize interface 156 to provide a data link 112 between medical device 104 and mobile device 114. Interface 156 may provide a hardwired connection, wireless connection, or a combination thereof between medical device 104 and other electronic devices. In some implementations, data link 112 may be a wireless connection between interface 156 of medical device 104 and an interface 120 of mobile device 114 (e.g., interface 156 communicates with measurement device 114 via a Wi-Fi, cellular, near-field, radio, Bluetooth, optical, or other form of wireless connection). Data link 112 may be bidirectional or unidirectional, according to various implementations. For example, mobile device 114 may transmit data and/or instructions to medical device 104 in response to receiving a request for data and/or instructions from medical device 104 or unprompted, according to various implementations.

Similar to medical device 104, mobile device 114 may also include a processor 116 and a memory 118, i.e., a processing circuit. Memory 118 may store instructions that, when executed by processor 116, cause processor 116 to execute some or all of the operations described herein. Mobile device 114 may monitor and/or otherwise communicate with medical device 104 continuously or periodically, according to various implementations. In certain implementations, the mobile device 114 may be a portable or handheld device such as a smartphone, a personal data assistant, a tablet computer, a laptop computer, or the like In some implementations, medical device 104 may be configured to utilize data and/or instructions data received from mobile device 114 to alert a healthcare professional and/or adjust its operation. For example, medical device 104 may generate an audible sound, to alert a healthcare professional to attend to the device 104 and/or subject 102. In another example, medical device 104 may adjust its control over the medical procedure based in part on data/instruction received. For example, if medical device 104 is an apheresis machine, medical device 104 may adjust a citrate infusion rate to subject 102 provided by an infusion pump and/or provide a bolus of saline to subject 102, based on a determination that the blood pressure of subject 102 has dropped below a threshold value. In this way, subject 102, mobile device 114, and medical device 104 may form a feedback control loop during the medical procedure.

Data captured and/or generated by mobile device 114 may be used for record keeping purposes, according to various implementations. For example, mobile device 114 may associate a timestamp with measurements taken from subject 102. Similarly, medical device 104 may associate a timestamp with data received from mobile device 114. In some implementations, server 124 may receive the data from mobile device 114 and/or from medical device 104 and store an electronic record of the reaction of subject 102 to the medical procedure. In some implementations, server 124 may also receive operational data from medical device 104 via network 122. Operational data may include any data indicative of the operational state of medical device 104 during the medical procedure. For example, the operational data may include, but is not limited to, a fluid flow rate, a citrate infusion rate, a dosage of substance administered to subject 102 (e.g., a dosage of medicament, saline, blood, blood component, anticoagulant, or other fluid). In some implementations, the operational data may be time stamped, allowing a record of the operation of medical device 104 to be generated. Medical device 104 may be configured to time stamp the operational data at periodic or intermittent intervals, e.g., at least every 10 minutes, at least every 15 minutes, etc.

Server 124 may be any form of computing device or set of computing devices configured to store and communicate electronic data. For example, server 124 may be a personal computer, a mainframe, a cloud-computing environment, or a data center. In some implementations, server 124 may be a portable electronic device, such as a smartphone, a personal data assistant, a tablet computer, a laptop computer, or the like. Server 124 may include a processing circuit that includes a processor 126 and a memory 128 that stores instructions for processor 126. Server 124 may also include interface 130 configured to communicate with network 122 via a wireless or hardwired connection, according to various implementations.

Network 122 may be any form of computer network that relays information between medical device 104, server 124, and/or measurement device 114. For example, network 122 may include the Internet and/or other types of data networks, such as a local area network (LAN), a wide area network (WAN), a cellular network, satellite network, or other types of data networks. Network 122 may also include any number of intermediary computing devices (e.g., computer, servers, routers, network switches, etc.) that are configured to receive and/or transmit data within network 122.

Server 124 may receive and store data generated by mobile device 114 and/or operational data generated by medical device 104 in memory 128, in some implementations. In further implementations, memory 128 may store information about subject 102 and provide subject data to medical device 104 and/or mobile device 114. For example, subject data may include demographics information about subject 102 (e.g., height, weight, gender, etc.), medical information about subject 102 (e.g., allergies, symptoms, diseases, medical conditions, etc.), or other information that may be provided to other electronic devices by server 124. In some implementations, medical device 104 may adjust its operation based in part on subject data received from server 124. Server 124 may also provide installation data to medical device 104 via network 122 (e.g., to install, update, and/or remove software loaded in memory 154 of medical device 104). Server 124 may be configured to communicate with medical device 104 and/or mobile device 114 via any number of different networking protocols. For example, server 124 may communicate with medical device 104 and/or mobile device 114 via an HTTP connection, FTP connection, SSH connection, a telnet connection, combinations thereof, or other similar networking protocols. In some implementations, server 124 may relay data between medical device 104 and another electronic device. For example, server 124 may be a device that communicates with medical device 104 within the same medical facility and relays information between medical device 104 and a server of the manufacturer of medical device 104 via the Internet.

Figure 2:
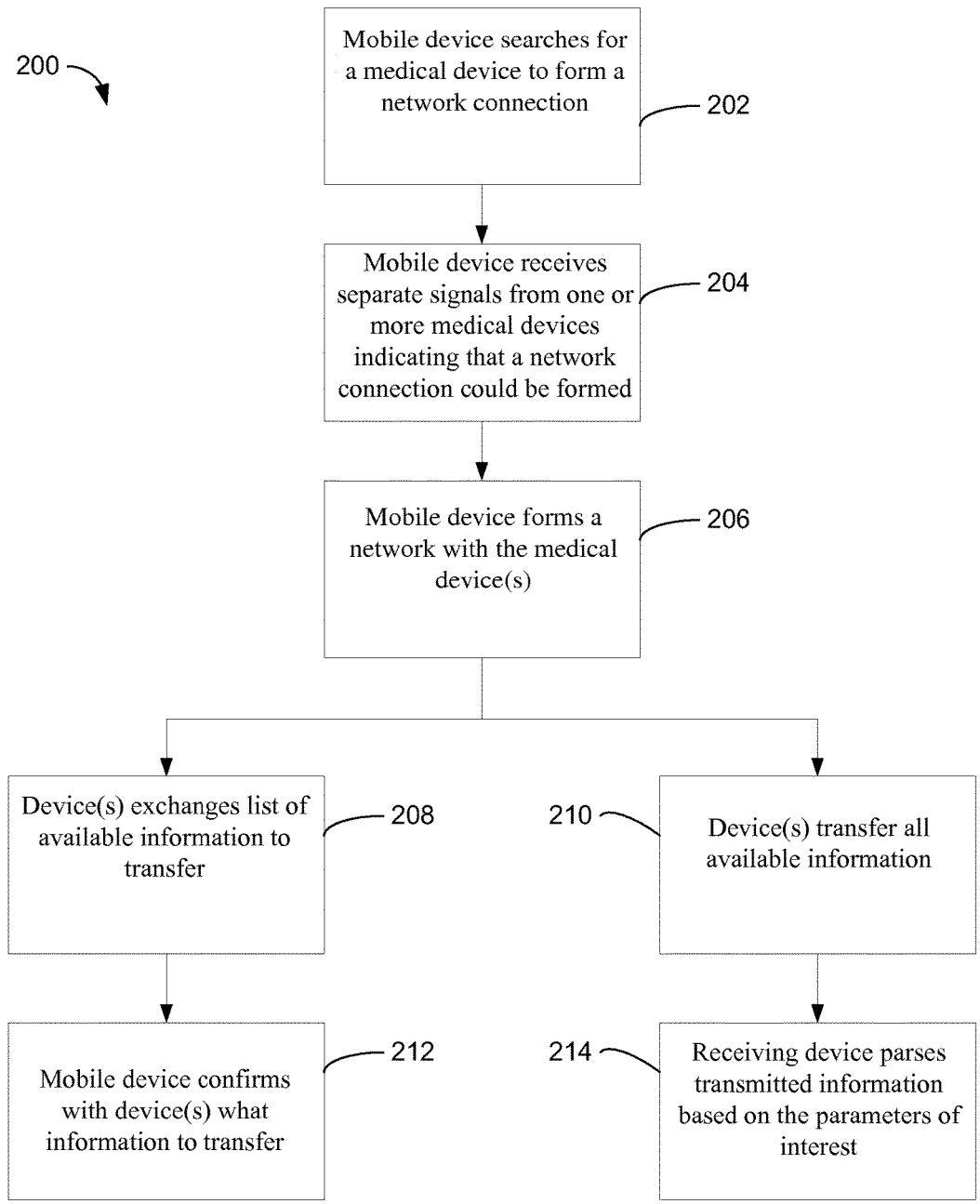
FIG. 2 is a flow diagram of an example process to interface a medical device with mobile device.

Referring now to FIG. 2, a process 200 for interfacing a medical device with one or more measurement devices is shown, according to various implementations. Process 200 may be utilized, for example, to interface medical device 104 of FIG. 1 with mobile device 114, in one implementation. While process 200 is shown with reference to a mobile device initiating a data connection with a medical device (e.g., an apheresis instrument, drug delivery system, etc.), the other device may initiate the connection in other implementations.

Process 200 may include a mobile device searching for a medical device to form a network connection (block 202). For example, the mobile device may search for an eligible infusion pump with which to interface. In some implementations, the mobile device may search for a medical device by broadcasting a wireless signal.

In some implementations, a security mechanism may control which devices are able to establish a data link. For example, an identifier of a mobile device may be registered with a medical device, or vice-versa, to determine eligibility to establish a data link. In some implementations, the identifier may be associated with a password. For example, the medical device may be utilized to send an identifier and password to a mobile device, to establish a data link between the devices.

Process 200 may include the mobile device receiving an indication from one or more devices that a connection can be formed (block 204). A device may not be eligible to establish a connection with a mobile device for any number of different reasons. For example, a medical device may be ineligible to interface with a mobile device because the device is turned off, is running a diagnostic routine, is in an error state (e.g., line blocked, pressure abnormality, air-in-line, bag empty, etc.), is not registered with the medical device, or the mobile device provides the wrong credentials to the medical device. If the medical device is active, ready to establish a connection, and/or the mobile device provides proper credentials, the medical device may return an indication that the data link may be formed.

Process 200 may include forming a network between the mobile device and the one or more medical devices (block 206). In some implementations, the network connection between the medical device and mobile device may be a direct connection. In other words, the data connection between the medical device and the mobile device may not go through any intermediary devices. In other implementations, the data connection may pass through one or more intermediary devices (e.g., computers, routers, switches, etc.) between the medical device and the mobile device to which it is connecting. For example, a medical device may interface with a smartphone via a Wi-Fi LAN of a medical clinic.

Process 200 may include one or more of the connecting devices providing a list of available information to the other connecting device(s) (block 208). The list may include some or all of the different types of data values available from the other device and/or other parameters to control the delivery of data to and/or operation of the medical device. In some cases, the list may include parameters that may be used by the medical device to control how often data values are to be provided to the medical device, the units of measure for the data values (e.g., Celsius vs. Fahrenheit, etc.), how often the other device is to measure a subject's vital signs or other physiological readings, or any other type of parameter. In some implementations, the list may be provided in response to a data link being established between the medical device and the other device. In other implementations, the list may be provided to the medical device in response to the medical device providing a request for available data to the mobile device.

Process 200 may include the mobile and/or medical device providing an indication of what information is to be transferred from one device to the other device (block 212). For example, the medical device may provide an indication to the mobile device that the subject's blood pressure is to be sent, but not the subject's pulse rate. In another example, the indication may specify that blood pressure readings are to be sent every thirty seconds to the medical device.

Alternatively, or in addition to block 208, 212, process 200 may include one device transferring all available data to the other device (block 210). In some implementations, the transfer of data may be automatic (i.e., without further user intervention), in response to a data connection being established. In other implementations, the medical device may provide data to the mobile device in response to receiving a request for the data. Whether the medical device provides the data immediately or allows the mobile device to select which data is provided may be controlled by a parameter, in some implementations. For example, a user of the medical device or other device may set a parameter to control how the two devices interface.

Process 200 may include a receiving (e.g., medical and/or mobile) device parsing the transmitted data based on parameters of interest (block 214). In cases in which one device provides all available data to the other device, the data may include extraneous data that is not of use to the receiving device. For example, the medical device may utilize blood pressure measurements, but not pulse rate measurements. If the other device provides both blood pressure measurements and pulse measurements to the medical device, the medical device may parse the received data to only utilize the received blood pressure measurements. In some implementations, the data of interest for a mobile and/or medical device may change over time (e.g., as a function of the current operating state of the medical device, based on a user-set parameter, etc.).

Figure 3:
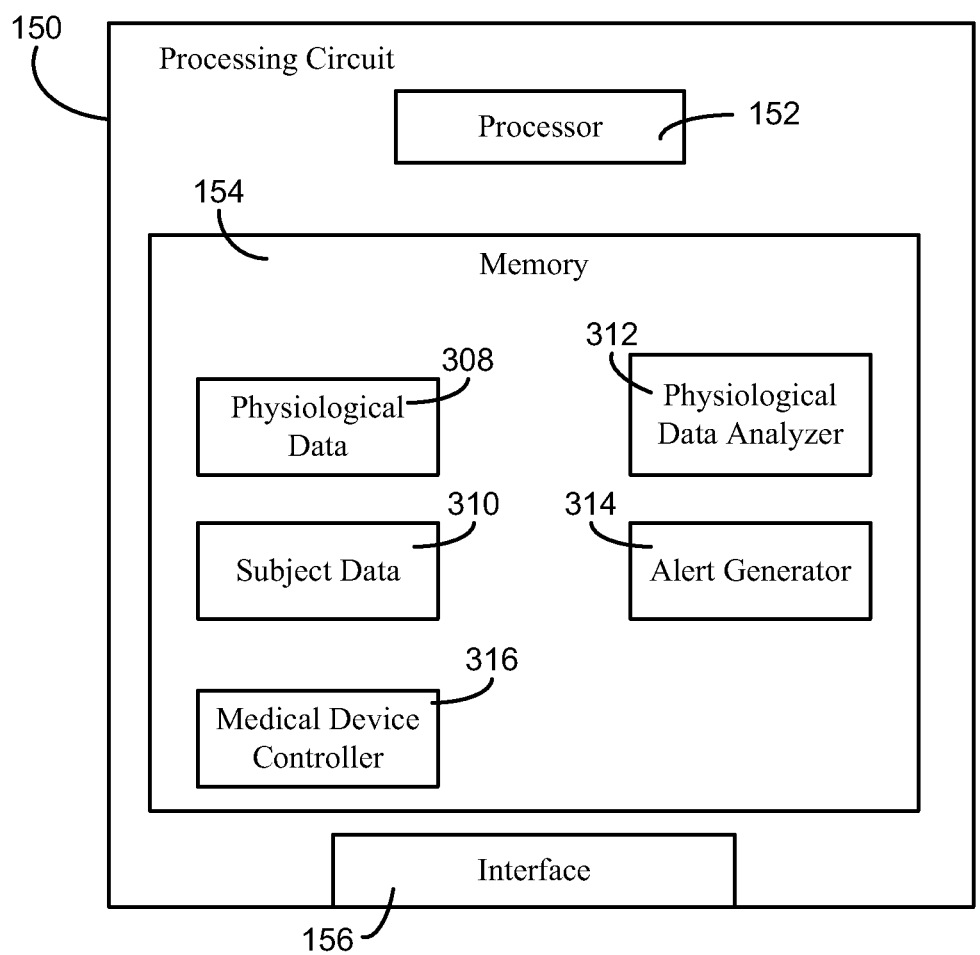
FIG. 3 is a block diagram of an example processing circuit of a medical device and/or mobile device.

FIG. 3 illustrates a processing circuit for a device, such as medical device 104 and/or mobile device 114. In some implementations, medical device controller 316 may generate operational data indicative of the operational state of the medical device. For example, medical device controller 316 may record data relating to actions performed by the medical device and/or control commands issued by medical device controller 316. In some cases, the operational data may be time stamped by medical device controller 316. For example, medical device controller 316 may record when a bolus of saline was provided to a subject. In this way, a record of the operation of the medical device may be created. Processing circuit 150 may provide the operational data and/or physiological data 308 to another electronic device, such as an electronic display or a networked server.

Memory 154 may include alert generator 314, in some implementations. Similar to medical device controller 316, alert generator 314 may generate an alert based in part on the analysis of physiological data 308 by physiological data analyzer 312. For example, alert generator 314 may generate an alert if the subject's blood pressure drops below a certain threshold. In various implementations, an alert may be generated by alert generator 314 in addition to, or in lieu of, medical device controller 316 adjusting an operation of the medical device.

In some cases, an alert generated by alert generator 314 may be provided to a user interface device via interface 156. For example, alert generator 314 may cause a sound to be produced by a speaker. In another example, alert generator 314 may cause indicia to be displayed on an electronic display. In further cases, an alert generated by alert generator 314 may be provided to a mobile device 114 operated by a healthcare professional (e.g., as a text message, status alert, automated phone call, etc.). In this way, a healthcare professional may be alerted if the subject has an adverse reaction to the medical procedure, the device malfunctions, a kit needs to be installed, etc.

Processing circuit 150 may communicate with a remote device via interface 156 to perform any number of functions. In some implementations, operational data 524 may be transferred from medical device 104 to a remote device (e.g., mobile device 114) for storage, control, and/or service of medical device 104. For example, a technician may analyze the received operational data to debug any potential problems during the operation of medical device 104. Since the data stored in memory 154 is segregated, operational data may be transferred remotely even during the performance of a medical procedure, without significantly impacting the medical procedure. In one example, procedure data may be generated as an XML file when one of medical procedure routines is executed, transferred to one partition from another partition, and transferred to a remote device during execution of the routine. In a further example, the entirety of procedure data may be transferred to operational data after completion of the medical procedure and relayed to a remote device via interface 156. In some implementations, installation data may be transferred to medical device 104 from the remote device via interface 156. For example, a technician may operate a device to make software and/or configuration changes to medical device 104 by installing, updating, or deleting certain software from medical device 104 via interface 156. In another example, the technician may update subject data 310 via a remote device (e.g., after the subject of the procedure checks in, information regarding the particular subject may be downloaded to the medical device for use during the procedure). In some implementations, some or all of the data transferred between processing circuit 150 and a remote device may be encrypted and sent over a secure connection.

The transfer of data between processing circuit 150 and a remote device via interface 156 may utilize a push or pull methodology. In some implementations, processing circuit 150 may transfer operational data to a remote device in response to receiving a request for the data from the remote device. For example, a technician may operate the remote device to request log files and other forms of diagnostic data from processing circuit 150. Similarly, a user may operate medical device 104 to request software updates and other types of configuration data from a remote device. In other implementations, data may be transferred between processing circuit 150 and a remote device via a push methodology (i.e., without first receiving a request for the data from the other device). For example, operational data may be transferred to a remote device in real-time, when operational data is stored in a partition. In some implementations, software qualification may be required to access memory 154 via a remote device. In other words, a software program running on the remote device requesting access to memory 154 may only be allowed access if it has valid credentials.

Figure 4:
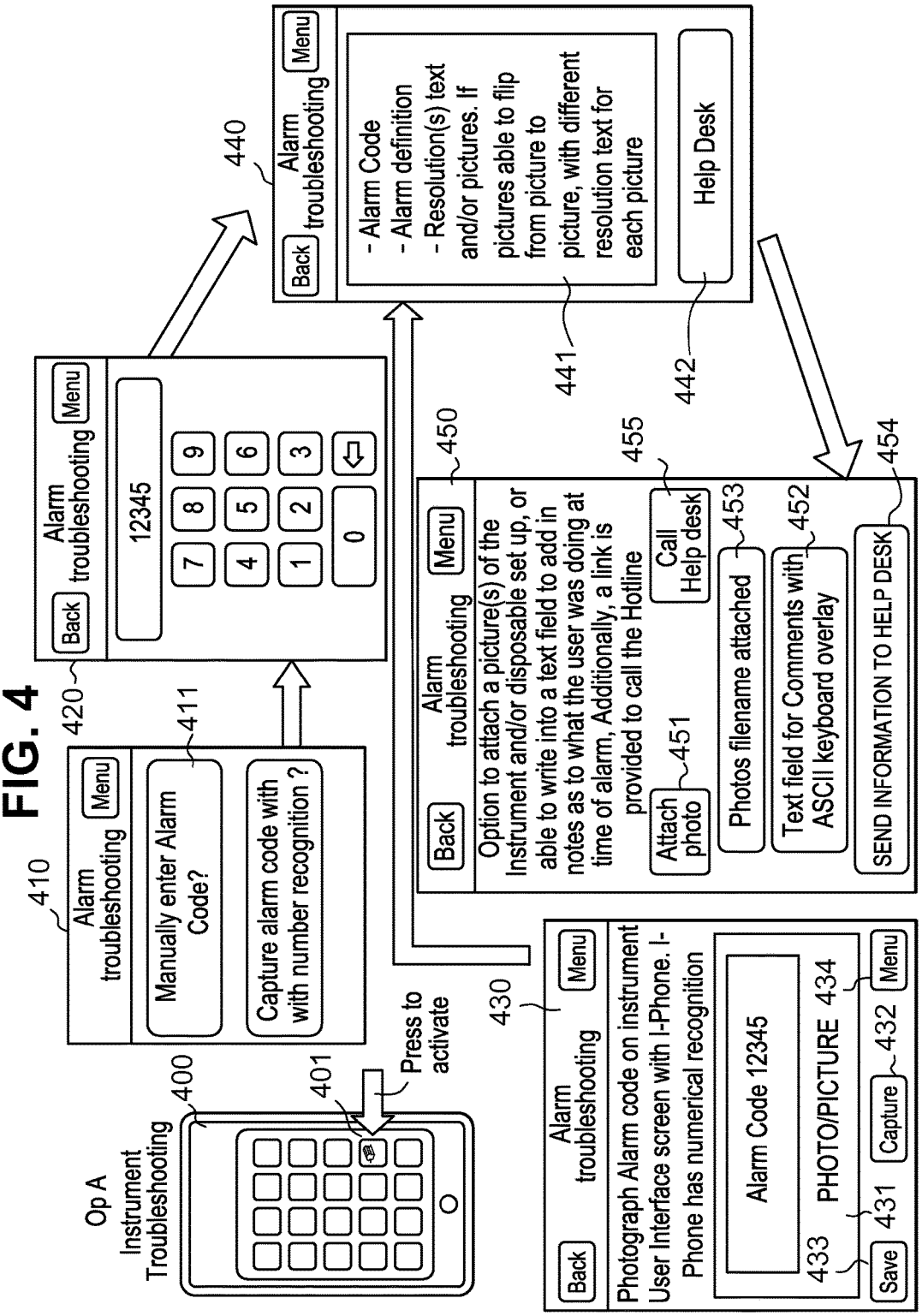
FIGS. 4-6 show example interfaces for blood collection device operators.
Figure 5:
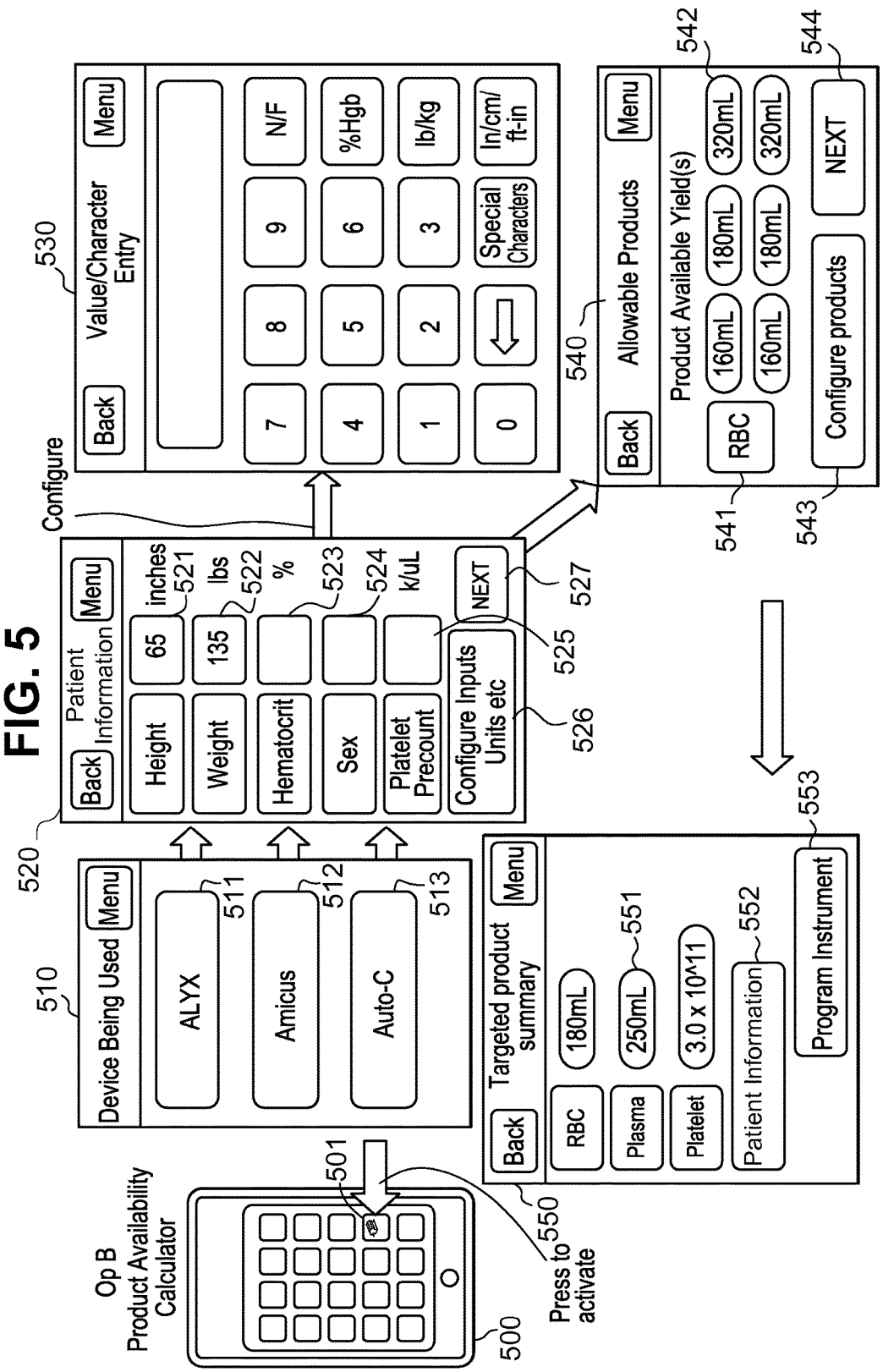
Figure 6:
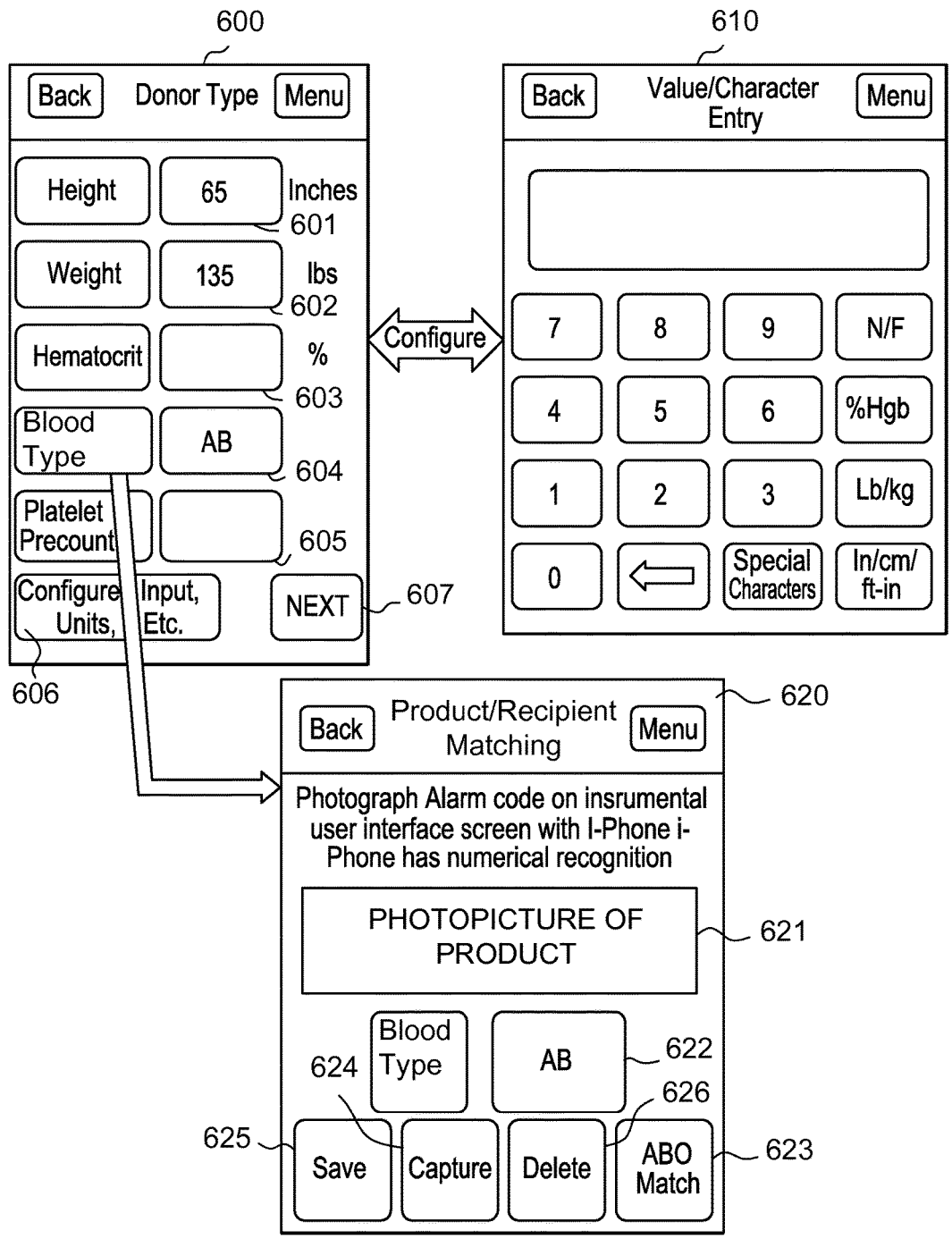

FIGS. 4-6 show example interfaces for medical device operators (e.g., with respect to Operators A-C). For an operator, an example application can provide instrument troubleshooting and/or other interaction. For example, the operator can enter an alarm code or take a picture of the alarm screen or disposable or other kit configuration. The application can present possible solutions; provide video(s) to resolve issue(s) if needed/desired/configured; use picture recognition and help access kit setup issues and provide resolutions; link to a hotline; etc. One or more representations (e.g., graphical representations such as alphanumeric indicators, icons, boxes, etc.) of one or more medical devices can be provided via the interface on a mobile device (e.g., a smartphone, personal digital assistant (PDA), handheld computer, laptop computer, etc.) to allow a user to select, retrieve information for, and/or provide instruction to one or more selected devices via the representation(s).

In certain examples, the application can provide blood products available to be collected based on donor characteristics. The application can communicate how long the collection would take and the number of people helped based on the collection, for example. In other examples, the application can provide drugs and/or other fluids available to be administered or otherwise delivered to a patient. The application can communicate a dosage, time period, and/or other constraints for the drug delivery, for example. The application can allow for the transfer of procedure information and log files from an instrument using a communication protocol/medium such as WI-FI™, BLUETOOTH™, etc. In certain examples, the application can trigger/push instrument alarms or procedure information to an operator (e.g., receive a text message when an alarm occurs and provide links to troubleshooting if needed/desired/configured). The application can provide a real time scorecard (e.g., a goal was to collect 15 units with an average turnaround time of 55 minutes, to deliver 500 ml of a drug at a flow rate of 100 ml/h, etc.). The application can keep track of progress and report it back to an Administrator, for example. An operator can also see a "scoreboard" on how the operators/teams are doing, e.g. team competitions. The application can enable the operator to photograph a label on a product bag or disposable kit and check to help ensure that the supply matches the donor or recipient, for example.

As shown, for example, in FIG. 4, a computing device 400, such as a smartphone or other computer, can provide an operator application 401. The application 401 can include an alarm troubleshooting interface 410 to assist a device operator in troubleshooting an alarm or error triggered at a medical device (e.g., a blood collection instrument, infusion pump, syringe pump, intravenous (IV) pump, etc.), for example. The alarm troubleshooter 410 can provide the operator with an option to enter an alarm code 411, such as via a keypad 420. The alarm troubleshooter 410 can also provide the operator with an option to capture an alarm code with number recognition 412, such as via a capture screen 430. The capture screen 430 shown in the example of FIG. 4 allows a user to capture, such as using a phone and/or other camera device, an alarm code shown on a medical device 431. Via the capture interface 430, the user can capture 432, save 433, and/or delete 434 a captured image with code 431.

Following input of an alarm code, either through manual entry or photo capture, an alarm troubleshooting guide 440 is displayed. The troubleshooting guide 440 provides information 441 including an alarm definition for the alarm code along with materials to help the user resolve the alarm. For example, text and/or images to assist the operator in resolving the device alarm can be provided via the interface 440. The operator can use the interface 440 to flip between a series of pictures/images along with supporting resolution text for each picture to resolve the alarm, for example. A help desk option 442 can be provided to assist the operator in resolving the alarm, for example.

Selecting the help desk option 442 brings the operator to a help desk screen 450. The help desk screen 450 provides the user with an opportunity to attach a photograph 451 of an instrument and/or disposable set up at issue. The user can also provide information via a text field 452 regarding the problem. A listing of photos and/or files attached 453 can be provided for user confirmation, and the user can submit 454 the information to the help desk. Additionally, an option can be provided for the user to call the help desk 455.

FIG. 5 depicts an example product availability calculator 501 available via a mobile and/or other computing device 500. The calculator 501 provides a view 510 of devices being used at a facility, such as an apheresis device, an infusion pump, a syringe pump, and/or other device. While an ALYX™ system 511, an AMICUS™ separator 512, an AUTOPHERESIS-C™ system 513 are shown for purposes of illustration only, other medical devices such as an OPTIMA™ pump, a PILOT™ pump, an AGILIA™ pump, and/or other drug delivery system can be evaluated and controlled as well. Selecting any of these devices 511, 512, 513 launches a donor or patient information screen 520. The patient/donor information view 520 includes a plurality of values, such as height 521, weight 522, hematocrit 523, sex 524, platelet precount 525, etc., for the person who is receiving medicament, donating blood, etc.

Patient values 521-525 can be color-coded, for example, for easy identification of their status. For example, green indicates that a parameter value has been entered. Yellow indicates that a parameter value has not been entered but is required, for example. Blue indicates that a parameter value has not been entered but is optional, for example. A value 521-525 can be selected to display a keypad 530, for example, to enter the parameter value. In certain examples, the keypad 530 can only show allowable values and/or other options for a given parameter 521-525. Additionally, an option 526 can be provided to configure one or more inputs, units, etc., associated with the donor values 521-525.

Selecting a next option 527 provides a list of allowable products (e.g., blood products, drugs, IV fluids, etc.) 540 based on the donor parameter values 521-525. For example, based on entered and/or retrieved donor parameter values 521-525, a given product can be made available 541, along with one or more available yields or dosages 542. One or more products can be made automatically and configured 543 based on a selected instrument, for example.

Selecting next 544 presents a targeted product summary 550 including one or more products 551 and associated amounts, for example. Donor information 552 can again be accessed, for example. An instrument can be programmed 553 based on the donor and product information, for example.

FIG. 6 illustrates an example patient or donor type configuration interface 600. The screen 600 includes a plurality of patient parameters, such as height 601, weight 602, hematocrit 603, blood type 604, platelet precount 605, etc. Values 601-605 can be entered using a keypad 610, for example. A configuration option 606 for inputs, units, etc., can be provided. A user can also access a product/patient matching interface 620. Using the matching interface 620, an operator can photograph a label on a product bag, for example, and the label is checked to help ensure that the product (e.g., blood product, drug, IV fluid, etc.) and recipient are correct and that the bag was correctly labeled.

As shown in the patient/product matching screen 620, a picture of a product bag label 621 is provided along with a patient identifier (e.g., donor blood type, patient identification number, etc.) 622. When ABO match 623 is selected, for example, the system either accepts the match or indicates that an ABO match has not been found (e.g., via flash, sound, message, etc.). The interface 620 allows an image to be captured 624, saved 625, deleted 626, etc.

Figure 7:
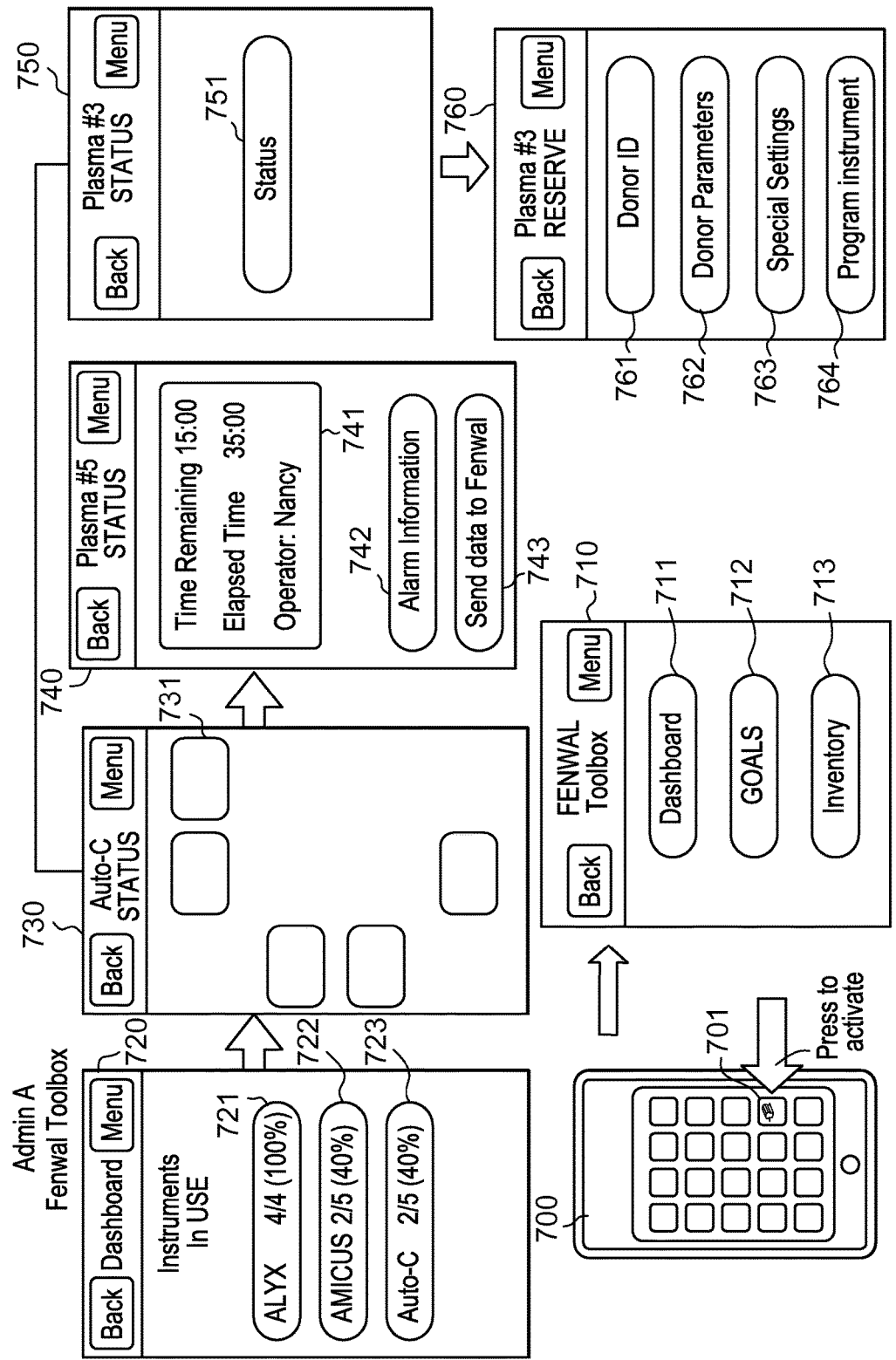
FIGS. 7-8 illustrate example interfaces for blood center administrators.
Figure 8:
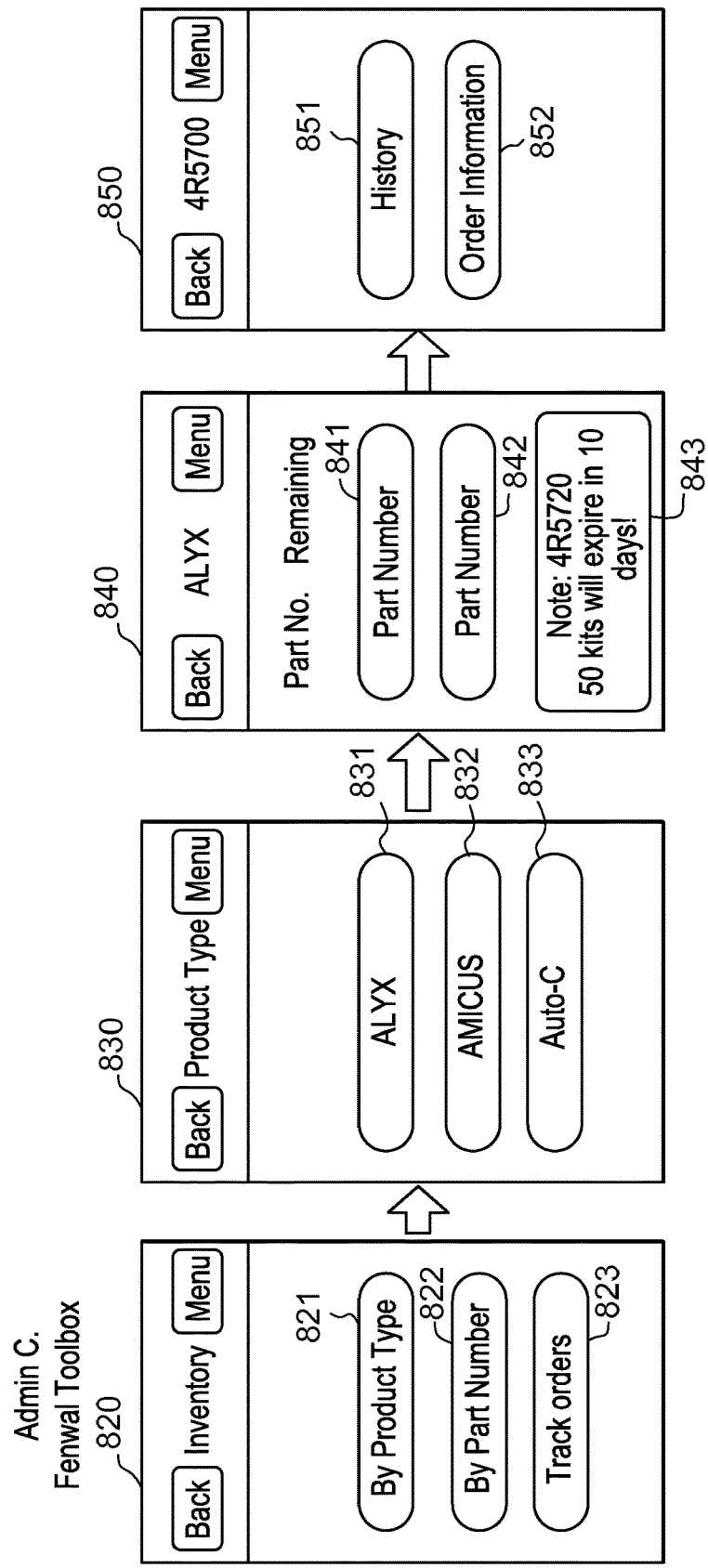

FIGS. 7-8 illustrate example interfaces for healthcare facility administrators (e.g., with respect to Administrators A-B). For an administrator, an example application can provide a booking/scheduling tool, supplies, needed, demand, available timing for instruments, etc. The application can push announcements from the administrator to patients/donors and/or operators regarding upcoming events and/or desired for delivery/collection. The application can be used to submit complaints or issues experienced using simple forms with an ability to submit photos of issues.

FIG. 7 depicts an example mobile device 700 including an administration application 701 for facility and/or medical device administrators. The application 701 provides a toolbox 710 including a dashboard 711, goals 712, inventory 713, etc. Selecting the dashboard 711, for example, provides a dashboard view 720, including one or more instruments in use, such as an ALYX™ system 721, AMICUS™ separator 722, and AUTOPHERESIS-C™ system 723 (and/or an OPTIMA™ pump, a PILOT™ pump, an AGILIA™ pump, and/or other drug delivery system).

Selecting an instrument, such as an OPTIMA MS™ pump, provides a status view 730 for the selected instrument. The status view 730 includes a layout 731 of one or more instruments at a facility, for example. The screen layout 731 can match a room layout, for example. One or more colors and/or other indicators can be used to determine instrument status (e.g., in-use, available, instrument alarm, etc.).

Selecting a particular instrument from the layout 731 provides more detailed status information 740 for that device. The device status provides additional information 741 regarding a procedure being executed at the selected device, such as time remaining, elapsed time, operator, etc. Additional information regarding the procedure can be displayed, such as a product volume collected graph, drug volume dispensed graph, etc. Information on one or more active alarms 742 for the device can also be provided, for example. Information can be sent to Fenwal 743, for example.

Instrument interface 750 depicts another example device interface for a device (e.g., Autopheresis-C™ Plasma #3, OPTIMA VS™, etc.) that provides a status 751 of available (versus unavailable, error, busy, etc.). A user can select the status 751 to reserve and program the device via the interface 760. Via the example reservation interface 760, the user can specify a patient identifier 761, patient parameters 762, special settings 763, etc., to provide a program to the instrument 764.

Using the administrator toolbox 710, the user can also select goals 712 to enter one or more goals for drug delivery, IV fluids, blood transfusion, blood collection, etc. (e.g., according to a treatment plan for a patient).

Using the administrator toolbox 710, the user can also select inventory 713 to access an inventory interface 820, as illustrated in the example of FIG. 8. The inventory view 820 provides a view or representation of instruments by product type 821, part number 822, etc., and/or track orders 823. Selecting product type 821, for example, provides a product type listing 830, including, for example, Alyx™ system 831, AMICUS™ separator 832, Autopheresis-C™ system 833, etc. (and/or an OPTIMA™ pump, a PILOT™ pump, an AGILIA™ pump, and/or other drug delivery system). Selecting a product type provides a detail view 840 for the selected product, including one or more part numbers 841, 842 along with a number of kits remaining. A note, alert or reminder 843 can be provided, such as a note reminding the administrator that 50 kits for a part number will expire in 10 days. The user can select a part number 841, 842 to view additional information regarding that part 850. From the part view 850, the user can review a history 851, order information 852, etc. for the part.

Certain examples provide a dashboard application that can provide status of instrument(s) on the floor, alarms, infusion/delivery status, time remaining, instrument turns, idle time, etc. A dashboard can also provide for the end of the day summaries. The dashboard can provide an ability to forward this information to a provider (e.g., Fenwal) if servicing is needed/desired/due.

An application can push patient information to an instrument to pre-program the instrument with patient preferences (e.g., smaller veins so the application sets the instrument at a slower flow ratio). The application can be configurable by a facility, for example. The application can push reminders and/or alerts regarding guidelines, best practices, etc., such as to alert an operator or patient that the patient has left a facility too soon after treatment, for example.

Example applications provide an inventory management tool including kits used, kits remaining, etc., and can push notices for expiry of upcoming kits; link or push notification for ordering new inventory; allow for the photographing of a barcode to recall inventory data, etc.

For a provider, certain examples can help provide operator application, service troubleshooting, issue resolution help and/or enable proactive maintenance. For sales, an application can help track customer performance and usage rates, sales trends, complaints, etc. An application can be provided for new sales training, new publications, market data trends, events, etc.

In some examples, an application can give visual assistance in operating a drug delivery system or other medical device. In some examples, the application may provide a mobile version of the operator's manual for the medical device.

In some examples, an application may make provider websites mobile-friendly. For example, Microsoft SHAREPOINT™ supports mobile views and can be leveraged to provide a mobile-friendly provider (e.g., Fenwal) website.

Figure 9:
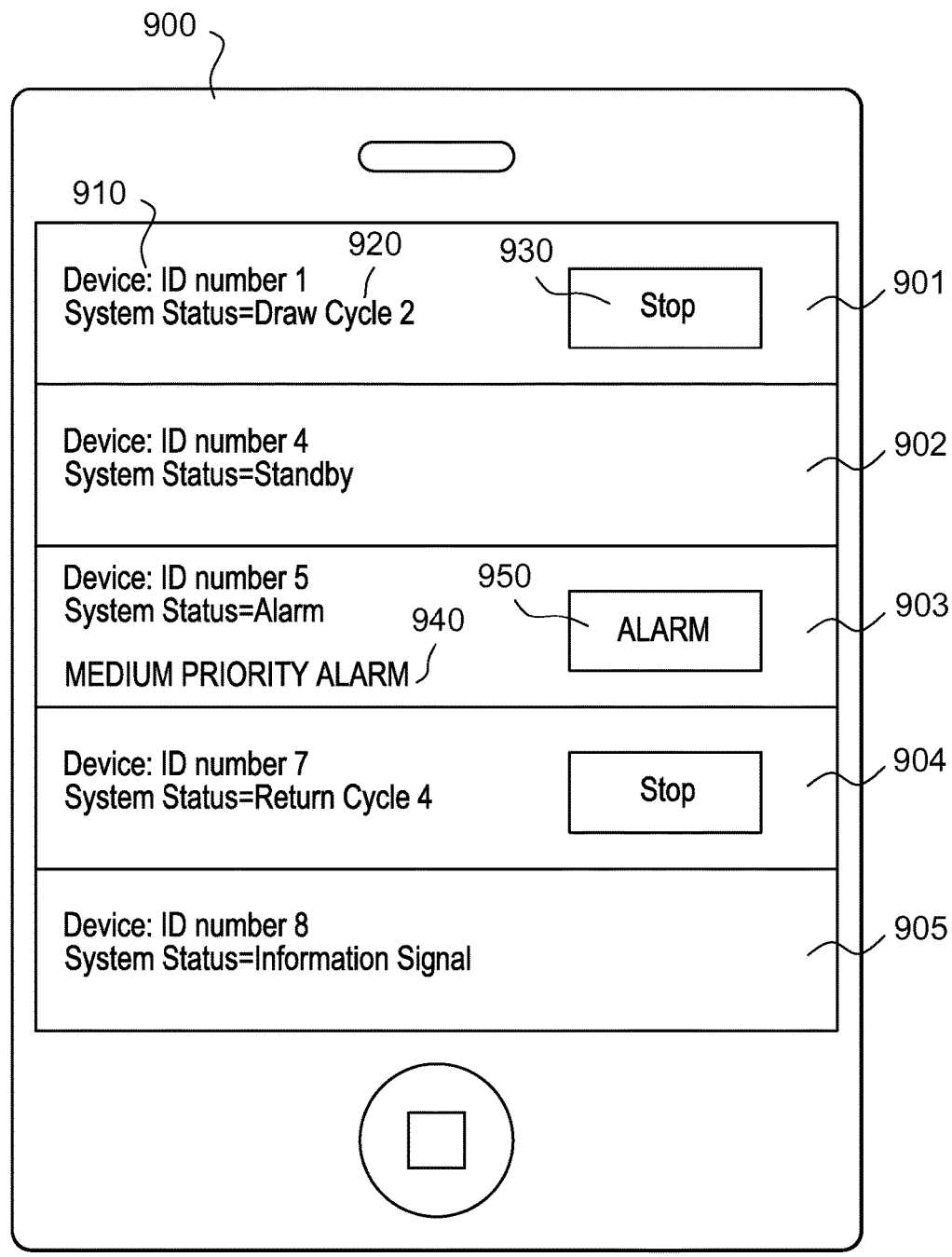
FIG. 9 depicts an example mobile device including an interface listing one or more blood collection/processing instruments under control of the operator.

FIG. 9 depicts an example mobile device 900 including an interface listing one or more medical devices 901, 902, 903, 904, 905 (e.g., blood collection/processing instruments, drug delivery systems, and/or other medical devices) under control of the operator. A device identifier 910 or other representation and status 920 is provided for each instrument 901-905. A control 930 can be provided to stop operation of the instrument 901-905, for example. If an alarm has been triggered at an instrument 901-905, an indication of the alarm 940 can be provided as well as an option for additional alarm information 950.

Thus, using the example mobile interface of FIG. 9, system status for all collection systems in a network can be provided to a mobile device 900, such as an IPHONE™, IPAD™, BLACKBERRY™, and the like. The status can include an instrument number, status, etc., and can provide quick access to one or more features such as a stop feature, an alarm feature, etc. The mobile device 900 can be used as a mobile monitor rather than tying an operator to a stationary desktop or computer system.

In certain examples, the mobile device 900 can provide a practice forum for training new operators regarding configuration, use, and/or troubleshooting of medical device(s). For example, step-by-step photos, diagrams, and instructions can be shown for proper disposable kit loading for one or more devices. Access to on-line operator's manuals, error codes, and/or product information can be provided via keyword search through the mobile device 900. In certain examples, complaints can be submitted via the mobile device interface 900. In certain examples, troubleshooting of instrument operation can be facilitated using the mobile device 900.

In some examples, an application enables a facility and/or device operator to report an issue (e.g., problem, complaint, etc.) to a provider (e.g., Fenwal).

Certain examples provide complaint reporting. Rather than a paper report, an operator who experienced an issue first-hand can submit a report and improve a likelihood of including important detail. The operator can register the complaint first hand and incorporate product bar code scans and photos that may be important to a complaint investigation. Pre-population of information can streamline the complaint reporting process, and automatically submitting the report to a vendor via the mobile device 900 can help save the trouble and time of faxing the document. Automatic assignment of a complaint number provides improved ability to track the complaint through to resolution.

In certain examples, an instrument trouble shooting decision tree can improve a speed with which an operator is able to resolve an issue rather than potentially delay to make a phone call and find an appropriate person with whom to speak. Also, submitting a service request can be more easily facilitated via the mobile device 900.

In certain examples, a camera associated with the mobile device 900 can be used to scan a product barcode as well as record and submit photo(s) of a complaint issue with the product to facilitate complaint description and filing. The camera can be used to record and submit instrument screen photo(s) with associated error code(s). Barcode scanning of the product retrieves a correct product complaint form that has been pre-populated with product information. The mobile interface can be used to additionally pre-populate the complaint form with center information, date, time, complaint reference number, etc. The mobile device 900 can be used to submit the complaint directly to the instrument vendor with an option to copy the facility's e-mail for local tracking, for example.

An additional feature can be an instrument trouble shooting decision tree similar to the practice currently used orally via instrument vendor customer service. The decision tree can help the operator 1) resolve the issue or 2) submit a service request either by a) embedded form or b) leading the user to call customer service directly from the mobile application.

In some examples, an application enables the catalog of products (e.g., Fenwal products) by selecting the product family and code number and the application will provide a complete product description such as quantity of bags in the set, type of sampling system, filter type (if applicable), solution types and volumes, etc; providing an electronic form to order products from customer service; and/or providing a database to track inventory levels by code/lot number/expiration date as products are received and shipped out to other centers or on mobile drives.

In some examples, an application enables product surveillance by snapping a picture of product defects and enabling a questionnaire(s) to be filled out; enabling complaints to be sent electronically to product surveillance; and/or receiving instructions on how to return the product for complaint investigation.

Figure 10:
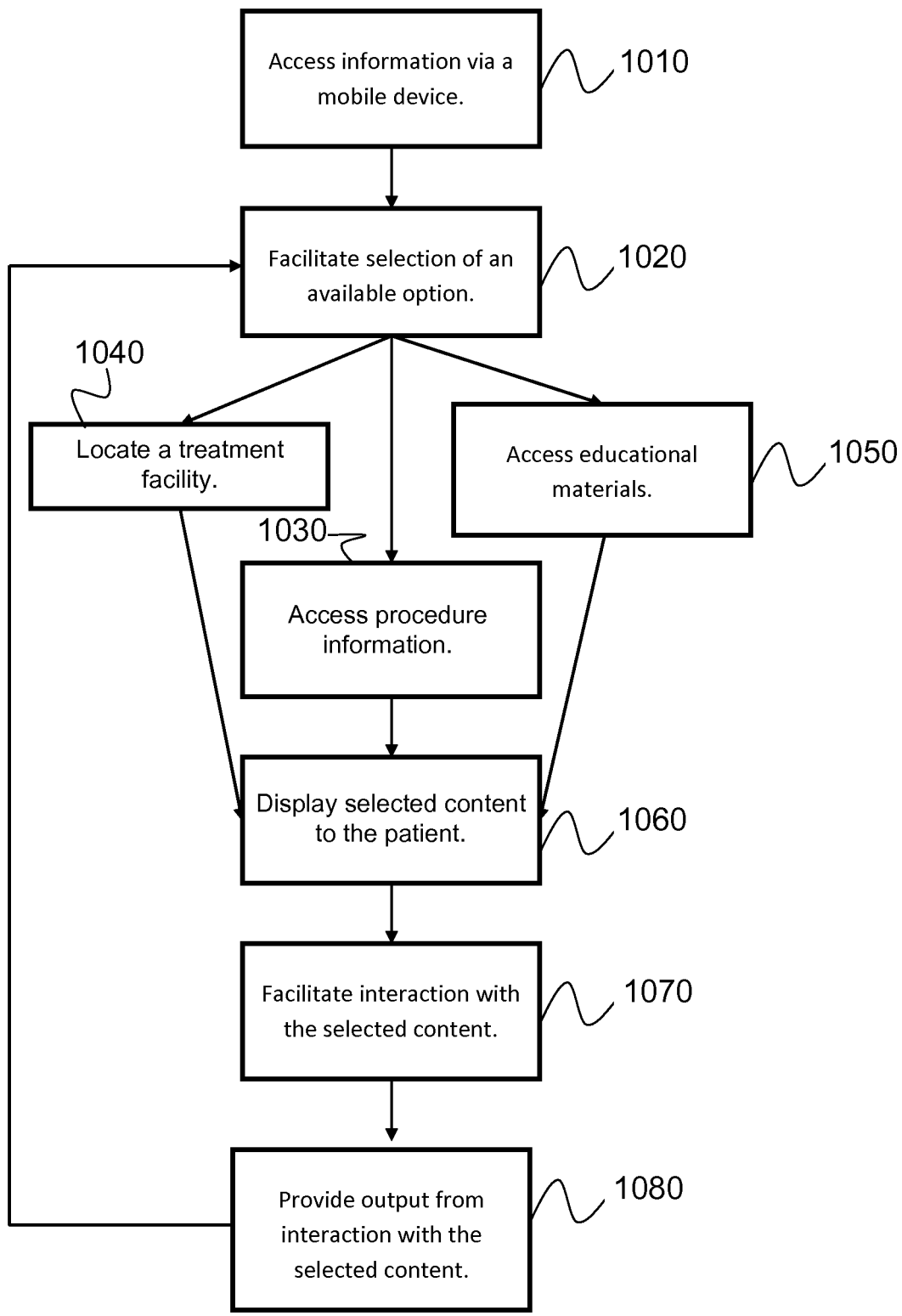
FIGS. 10-12 provide flow diagrams for methods for donors, operators, and administrators to review and manage blood collection and associated instrument information.
Figure 11:
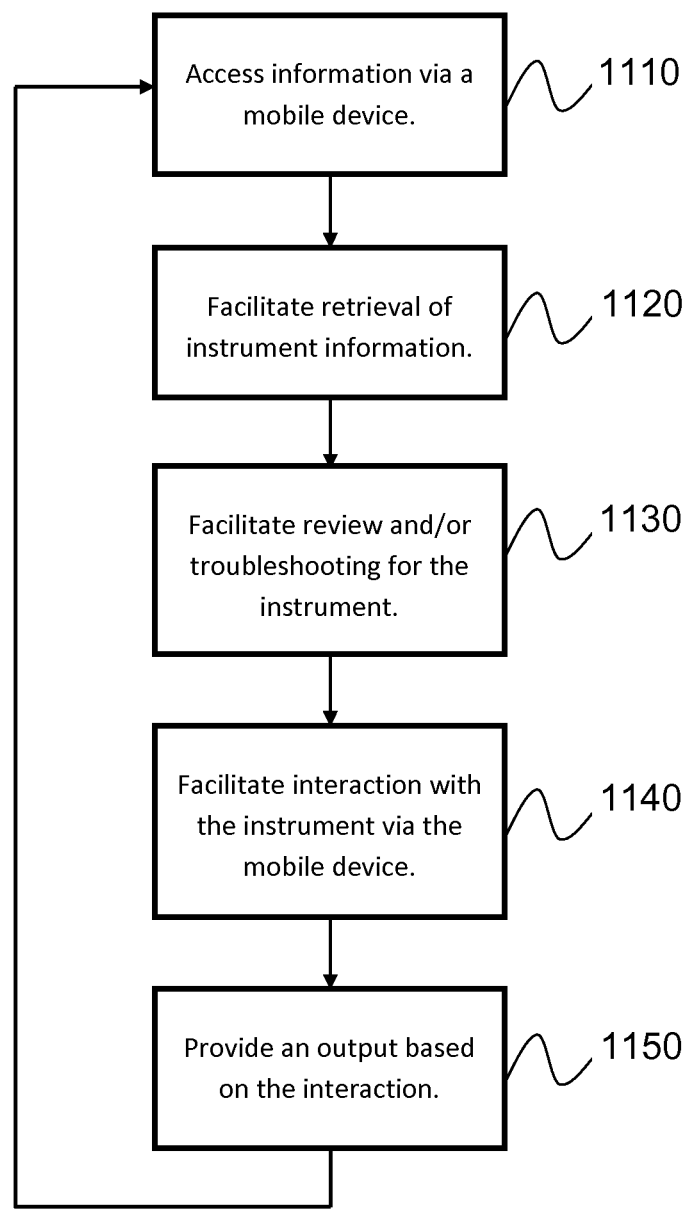
Figure 12:
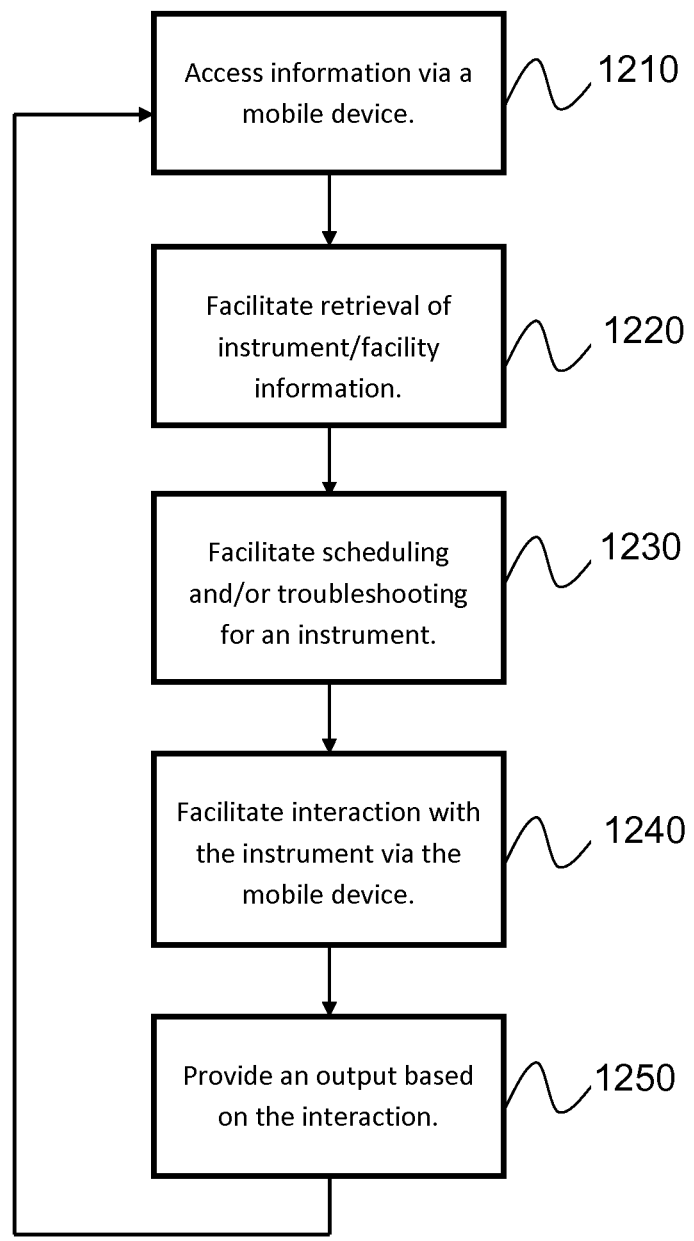

FIGS. 10-12 provide flow diagrams for methods for patients, operators, and administrators to review and manage blood collection and associated instrument information. FIGS. 10-12 depict example flow diagrams representative of processes that may be implemented using, for example, computer readable instructions that may be used during infusion pump operator training. The example processes of FIGS. 10-12 may be performed using a processor, a controller and/or any other suitable processing device. For example, the example processes of FIGS. 10-12 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 10-12 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 10-12 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 10-12 may be implemented manually or as any combination(s) of any of the foregoing techniques, for example, any combination of firmware, software, discrete logic and/or hardware. Further, although the example processes of FIGS. 10-12 are described with reference to the flow diagrams of FIGS. 10-12, other methods of implementing the processes of FIGS. 10-12 may be employed. For example, the order of execution of the blocks may be changed, and/or some of the blocks described may be changed, eliminated, sub-divided, or combined. Additionally, any or all of the example processes of FIGS. 10-12 may be performed sequentially and/or in parallel by, for example, separate processing threads, processors, devices, discrete logic, circuits, etc.

FIG. 10 provides a flow diagram 1000 for a method for donor access to procedure information (e.g., treatment for a particular diagnosis involving drug delivery). At block 1010, a patient accesses procedure information via a mobile device. The patient can be provided with a variety of information and functionality, such as facility location, procedure information, educational resources, etc. One or more medical devices can be displayed based on one or more associated graphical representations to allow a user to select, retrieve information for, and/or provide instruction to one or more selected devices via the representation(s), for example. At block 1020, the patient selects an available option. At block 1030, the patient views his or her procedure information via the mobile device. At block 1040, the patient locates a treatment facility via the mobile device. At block 1050, the patient accesses training/educational materials via the mobile device.

At block 1060, selected content is displayed to the patient via the mobile device. For example, procedure information is shown, a treatment facility is mapped, and/or educational materials are displayed for review and/or interaction. At block 1070, the patient user can interact with the displayed content. At block 1080, based on the interaction, an output is provided from the mobile device. For example, patient information can be updated, an appointment can be made, results can be sent, etc. The method can be executed in accordance with many examples, including examples described above.

FIG. 11 provides a flow diagram 1100 for a method for operator access to medical device information. At block 1110, an operator accesses instrument (e.g., infusion pump, syringe pump, other drug delivery instrument, etc.) information via a mobile device (e.g., via a graphical representation of the instrument displayed on the mobile device interface). At block 1120, instrument information is retrieved for operator review at the mobile device. At block 1130, the operator can review and/or troubleshoot the instrument via the mobile device. At block 1140, the operator can interact with the instrument via the mobile device. At block 1150, the mobile device provides an output based on the operator interaction with the instruction. The method can be executed in accordance with many examples, including examples described above.

FIG. 12 provides a flow diagram 1200 for a method for administrator access to medical device information. At block 1210, an administrator accesses healthcare facility information via a mobile device. At block 1220, facility and/or instrument (e.g., infusion pump, syringe pump, other drug delivery instrument, etc.) information is retrieved for administrator review via the mobile device. At block 1230, the administrator can perform a variety of activities, such as troubleshooting, scheduling, etc., with respect to one or more instruments in the facility. At block 1240, the administrator can interact with the one or more instruments via the mobile device. At block 1250, the mobile device provides an output based on the administrator interaction with the facility. The method can be executed in accordance with many examples, including examples described above.

Figure 13:
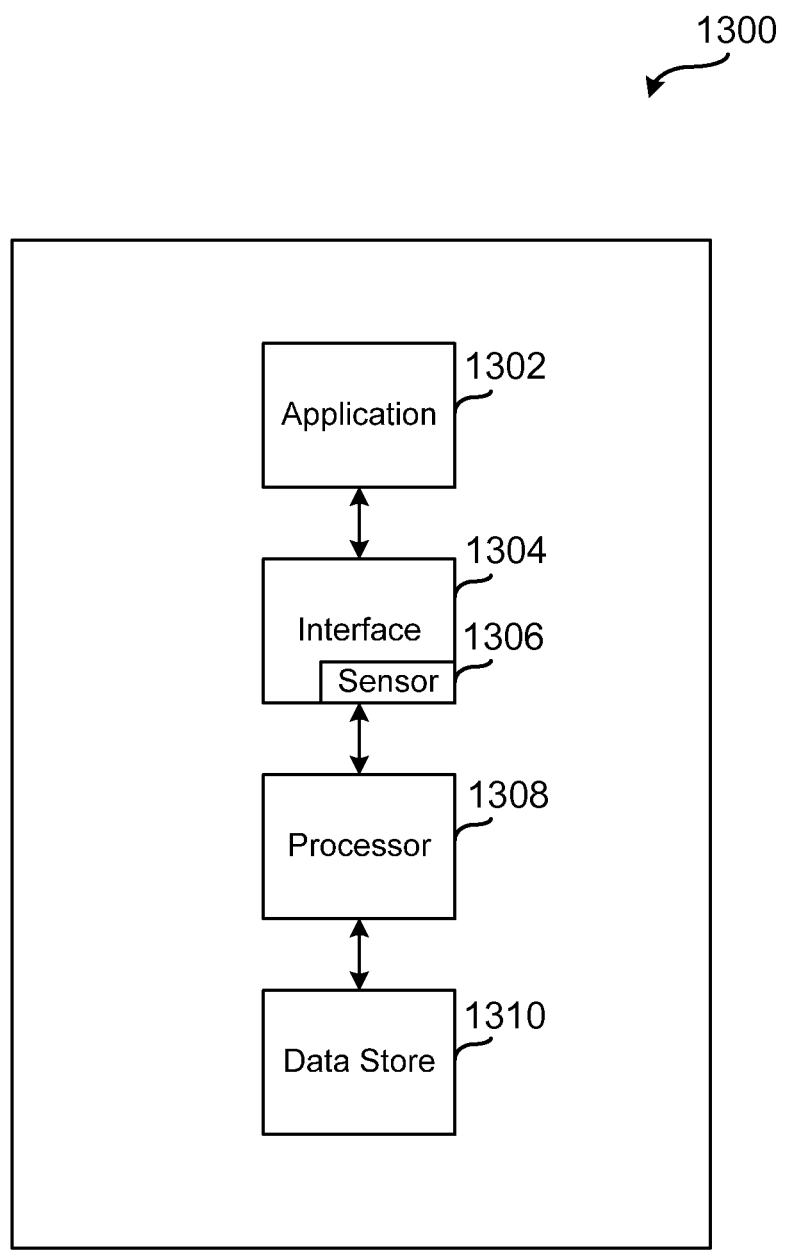
FIG. 13 is a block diagram of an example system or mobile device.

FIG. 13 is a block diagram of an example system or mobile device 1300 including an application 1302, an interface 1304 including a sensor(s) 1306, a processor 1308 and a data store 1310. The example system 1300 may be used to implement the example mobile devices described above, for example. While an example manner of implementing the mobile device has been illustrated in FIG. 13, one or more of the elements, processes and/or devices illustrated in FIG. 13 may be combined, divided, re-arranged, omitted, eliminated and/or implemented in other ways.

The application 1302, the interface 1304, the sensor 1306, the processor 1308 and/or the data store 1310 and, more generally, the example system 1300 may be implemented by hardware, software, firmware and/or a combination of hardware, software and/or firmware. Thus, the application 1302, the interface 1304, the sensor 1306, the processor 1308 and/or the data store 1310 and, more generally, the example system 1300 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the application 1302, the interface 1304, the sensor 1306, the processor 1308 and/or the data store 1310 and, more generally, the example system 1300 are hereby expressly defined to include a tangible medium such as a memory, DVD, CD, Blu-ray, etc., storing the software and/or firmware. Further still, the example system 1300 of FIG. 13 may include one or more elements, processes and/or devices in addition to, or instead of, those illustrated in FIG. 13, and/or may include more than one of any or all of the illustrated elements, processes and devices.

The application 1302 may include instructions that, when driven by the processor 1308, cause the processor 1308 to retrieve data, tutorial information, audio, graphics, text, etc. and display the same using the interface 1304. For example, based on the initiation of a tutorial session, the application 1302 may cause a video to be displayed on the interface 1304 on how to operate and/or troubleshoot a medical device. The application 1302 may cause instructions to be displayed on the interface 1304 on how to participate in the tutorial. In some examples, based on the system 1300 identifying the user's experience level, a different tutorial and/or information may be displayed. The system 1300 may identify the user's experience level from data stored at the data store 1310 and/or based on input received from the user.

Based on the information received, the processor 1308 may generate feedback that may be displayed at the interface 1304 and/or stored at the data store 1310. Once the processor 1308 determines that the tutorial is complete, the processor 1308 may generate feedback relating to the user's performance, etc. While the data store 1310 is depicted as being within the system 1300, the data store 1310 may be at a different location (e.g., a remote location).

The processor 1308 may drive the interface 1304 to provide information and/or functionality to the user. In some examples, the interface 1304 may be configured as a graphical user interface (GUI). The GUI may be touch pad/screen integrated with the system 1300. The system 1300 may include one or more internal memories and/or data stores including the data store 1310. Data storage can include any variety of internal and/or external memory, disk, remote storage communicating with the system 1300.

Figure 14:
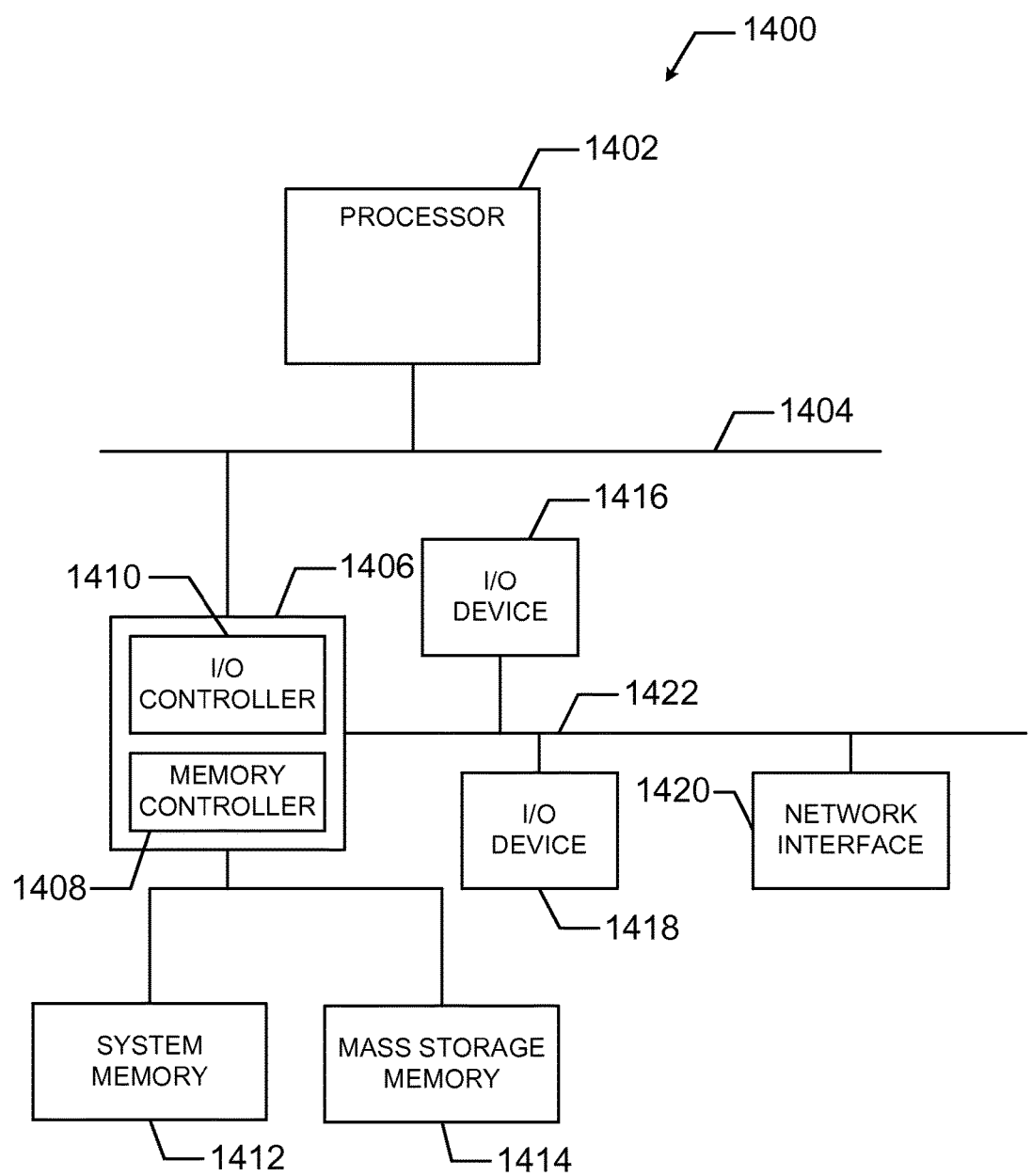
FIG. 14 is a block diagram of an example processor system that can be used to pump, implement, control and/or drive the systems and methods described herein.

FIG. 14 is a block diagram of an example processor system 1400 that can be used to pump, implement, control and/or drive the systems and methods described herein. As shown in FIG. 14, the processor system 1400 includes a processor 1402 that is coupled to an interconnection bus 1404. The processor 1402 may be any suitable processor, processing unit or microprocessor. Although not shown in FIG. 14, the processor system 1400 may be a multi-processor system and, thus, may include one or more additional processors that are identical or similar to the processor 1402 and that are communicatively coupled to the interconnection bus 1404.

The processor 1402 of FIG. 14 is coupled to a chipset 1406, which includes a memory controller 1408 and an input/output (I/O) controller 1410. As is well known, a chipset typically provides I/O and memory management functions as well as a plurality of general purpose and/or special purpose registers, timers, etc. that are accessible or used by one or more processors coupled to the chipset 1406. The memory controller 1408 performs functions that enable the processor 1402 (or processors if there are multiple processors) to access a system memory 1412 and a mass storage memory 1414.

The system memory 1412 may include any desired type of volatile and/or non-volatile memory such as, for example, static random access memory (SRAM), dynamic random access memory (DRAM), flash memory, read-only memory (ROM), etc. The mass storage memory 1414 may include any desired type of mass storage device including hard disk drives, optical drives, tape storage devices, etc.

The I/O controller 1410 performs functions that enable the processor 1402 to communicate with peripheral input/output (I/O) devices 1416 and 1418 and a network interface 1420 via an I/O bus 1422. The I/O devices 1416 and 1418 may be any desired type of I/O device such as, for example, a keyboard, a video display or monitor, a mouse, etc. The network interface 1420 may be, for example, an Ethernet device, an asynchronous transfer mode (ATM) device, an 802.11 device, a DSL modem, a cable modem, a cellular modem, etc. that enables the processor system 1400 to communicate with another processor system.

While the memory controller 1408 and the I/O controller 1410 are depicted in FIG. 14 as separate blocks within the chipset 1406, the functions performed by these blocks may be integrated within a single semiconductor circuit or may be implemented using two or more separate integrated circuits.

Certain examples can include processes that can be implemented using, for example, computer readable instructions that can be used to facilitate mobile applications relating to medical devices for patients, operators, administrators, and/or providers. The example processes can be performed using a processor, a controller and/or any other suitable processing device. For example, the example processes can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes can be implemented using coded instructions (e.g., computer readable instructions) stored on a non-transitory computer readable medium such as a flash memory, a read-only memory (ROM), a random-access memory (RAM), a CD, a DVD, a Blu-ray, a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes can be implemented manually or as any combination(s) of any of the foregoing techniques, for example, any combination of firmware, software, discrete logic and/or hardware. Further, although example processes may be described with reference to a particular order and/or structure, other methods of implementing the processes may be employed. For example, the order of execution of the blocks can be changed, and/or some of the blocks described may be changed, eliminated, sub-divided, or combined. Additionally, any or all of the example processes can be performed sequentially and/or in parallel by, for example, separate processing threads, processors, devices, discrete logic, circuits, etc.

While particular embodiments of the invention have been shown and described, it will be obvious to those skilled in the art that changes and modifications may be made therein without departing from the invention in its broader aspects.

The invention claimed is:

1. A computer-implemented method for medical device management using a handheld mobile device, said method comprising:

providing, via a handheld mobile device graphical user interface, a representation of one or more medical devices, the medical devices comprising at least one of a blood processing device, an infusion pump, and a drug delivery device, with a visual indication of a status for each medical device, the representation visually conveying information regarding each of the one or more medical devices and selectable by a user to provide additional information regarding each of the one or more medical devices;

updating the status for each medical device via wireless communication with the handheld mobile device;

facilitating troubleshooting of an alarm at one of the one or more medical devices by receiving an indication of an alarm code at the handheld mobile device via at least one of an entered alarm code and a captured image of an alarm condition, the alarm code representing an alarm or error condition of one or more of the medical devices; and providing information at the handheld mobile device to assist a user in handling the alarm or error condition of the one or more medical devices.

2. The method of claim 1, further comprising displaying an inventory of available products for the one or more medical devices at a healthcare facility and facilitating inventory control via the mobile device.

3. The method of claim 1, further comprising providing training to a medical device operator via the mobile device.

4. The method of claim 1, further comprising collecting and reporting an operator complaint via the mobile device.

5. The method of claim 1, further comprising facilitating product and patient matching via at least one of an entered value and a captured image using the mobile device.

6. The method of claim 1, wherein the one or more medical devices comprise one or more drug delivery devices.

7. The method of claim 6, wherein the one or more drug delivery devices comprise one or more infusion pumps.

8. The method of claim 1, further comprising controlling one or more medical device parameters via the mobile device, the one or more medical device parameters including one or more of patient physiological data, flow rate, infusion rate, volume limit, and pressure.

9. A tangible computer readable storage medium including program code for execution by a processor, the program code, when executed, to implement a method for medical device management using a handheld mobile device, said method comprising:
   providing, via a handheld mobile device interface, a representation of one or more medical devices, the medical devices comprising at least one of a blood processing device, an infusion pump, and a drug delivery device, with a visual indication of a status for each medical device, the representation visually conveying information regarding each of the one or more medical devices and selectable by a user to provide additional information regarding each of the one or more medical devices;
   updating the status for each medical device via wireless communication with the handheld mobile device;
   facilitating troubleshooting of an alarm at one of the one or more medical devices by receiving an indication of an alarm code at the handheld mobile device via at least one of an entered alarm code and a capture image of an alarm condition, the alarm code representing an alarm or error condition of one or more of the medical devices; and
   providing information at the handheld mobile device to assist a user in handling the alarm or error condition of the one or more of medical devices.

10. The computer readable storage medium of claim 9, wherein the method further comprises displaying an inventory of available products for the one or more medical devices at a healthcare facility and facilitating inventory control via the mobile device.

11. The computer readable storage medium of claim 9, wherein the method further comprises providing training to a medical device operator via the mobile device.

12. The computer readable storage medium of claim 9, wherein the method further comprises facilitating product and patient matching via at least one of an entered value and a captured image using the mobile device.

13. The computer readable storage medium of claim 9, wherein the one or more medical devices comprise one or more drug delivery devices.

14. The computer readable storage medium of claim 13, wherein the one or more drug delivery devices comprise one or more infusion pumps.

15. The computer readable storage medium of claim 9, wherein the method further comprises controlling one or more medical device parameters via the mobile device, the one or more medical device parameters including one or more of patient physiological data, flow rate, infusion rate, volume limit, and pressure.

16. A computer-implemented method for medical device management using a handheld mobile device, said method comprising:
   providing, via a handheld mobile device graphical user interface, a representation of one or more medical devices, the medical devices comprising at least one of a blood processing device, an infusion pump, and a drug delivery device, with a visual indication of a status for each medical device, the representation visually conveying information regarding each of the one or more medical devices and selectable by a user to provide additional information regarding each of the one or more medical devices;
   updating the status for each medical device via wireless communication with the handheld mobile device;
   receiving an indication of an alarm code at the handheld mobile device, the alarm code representing an alarm or error condition of one or more of the medical devices;
   providing information at the handheld mobile device to assist a user in handling the alarm or error condition of the one or more of medical devices; and
   displaying an inventory of available products for the one or more medical devices at a healthcare facility and facilitating inventory control via the mobile device.

* * * * *